United States Patent
Baruah et al.

(10) Patent No.: US 10,316,089 B2
(45) Date of Patent: Jun. 11, 2019

(54) PD-1 ANTIBODIES

(71) Applicant: Innovent Biologics (Suzhou) Co., Ltd., Suzhou (CN)

(72) Inventors: Hemanta Baruah, Lebanon, NH (US); Cheng Chen, Jiangsu (CN); Xiaolin Liu, Jiangsu (CN); Andy Tsun, Jiangsu (CN); Dechao Michael Yu, Jiangsu (CN)

(73) Assignee: INNOVENT BIOLOGICS (SUZHOU) CO. LTD., Suzhou (CN)

( * ) Notice: Subject to any disclaimer, the term of this patent is extended or adjusted under 35 U.S.C. 154(b) by 378 days.

(21) Appl. No.: 15/232,026

(22) Filed: Aug. 9, 2016

(65) Prior Publication Data
US 2017/0044260 A1    Feb. 16, 2017

(30) Foreign Application Priority Data
Aug. 10, 2015    (WO) ................ PCT/CN2015/086494

(51) Int. Cl.
*C07K 16/28*    (2006.01)
*A61K 39/395*    (2006.01)
*A61K 45/06*    (2006.01)

(52) U.S. Cl.
CPC .......... *C07K 16/2818* (2013.01); *A61K 45/06* (2013.01); *C07K 2317/70* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 7,563,869 | B2 | 6/2009 | Honjo et al. |
| 7,595,048 | B2 | 9/2009 | Honjo et al. |
| 7,851,598 | B2 | 12/2010 | Davis |
| 7,858,746 | B2 | 12/2010 | Honjo et al. |
| 2016/0272708 | A1 | 9/2016 | Chen |
| 2016/0376367 | A1 | 12/2016 | Yuan et al. |

FOREIGN PATENT DOCUMENTS

| EP | 3026062 A1 | 6/2016 |
| WO | 200114557 A1 | 3/2001 |
| WO | 2002079499 A1 | 10/2002 |
| WO | 2004056875 A1 | 7/2004 |
| WO | 2006042237 A2 | 4/2006 |
| WO | 2006121168 A1 | 11/2006 |
| WO | 2006133396 A2 | 12/2006 |
| WO | 2008156712 A1 | 12/2008 |
| WO | 2009067812 A1 | 6/2009 |
| WO | 2009114335 A2 | 9/2009 |
| WO | 2010029434 A1 | 3/2010 |
| WO | 2010029435 A1 | 3/2010 |
| WO | WO 2010/036959 A2 | 4/2010 |
| WO | 2012145493 A1 | 10/2012 |
| WO | WO 2012/135408 A1 | 10/2012 |
| WO | 2014179664 A2 | 11/2014 |
| WO | WO 2014/151006 A3 | 11/2014 |
| WO | 2014194302 A2 | 12/2014 |
| WO | 2015035606 A1 | 3/2015 |
| WO | 2015036394 A1 | 3/2015 |

OTHER PUBLICATIONS

Agata, Y. et al., "Expression of the PD-1 antigen on the surface of stimulated mouse T and B lymphocytes," International Immunology; 8(5), pp. 765-772 (1996).
Wang, C. et al., "In Vitro Characterization of the Anti-PD-1 Antibody Nivolumab, BMS-936558, and In Vivo Toxicology in Non-Human Primates," Cancer Immunology Research; 2(9), pp. 846-856 (Sep. 2014).
Freeman, G. et al., "Engagement of the PD-1 Immunoinhibitory Receptor by a Novel B7 Family Member Leads to Negative Regulation of Lymphocyte Activation," J. Exp. Med.; 192(7), pp. 1027-1034 (Oct. 2, 2000).
Ishida, Y. et al., "Induced expression of PD-1, a novel member of the immunoglobulin gene superfamily, upon programmed cell death," The EMBO Journal; 11(11), pp. 3887-3895 (1992).
Latchman, et al., "PD-L2 is a second ligand for PD-1 and inhibits T cell activation," Nature Immunology; 2(3), pp. 261-268 (Mar. 2001).
McDermott, et al., "PD-1 as a potential target in cancer therapy," Cancer Medicine; 2(5), pp. 662-673 (2013).
Yasuda, et al., "Simultaneous blockade of programmed death 1 and vascular endothelial growth factor receptor 2 (VEGFR2) induces synergistic anti-tumour effect in vivo," Clinical & Experimental Immunology; v172, pp. 500-506 (2013).
Zitvogel & Kroemer, "Targeting PD-1/PD-L1 interactions for cancer immunotherapy," OncoImmunology; 1(8), pp. 1223-1225 (Nov. 2012).

*Primary Examiner* — Ilia I Ouspenski
(74) *Attorney, Agent, or Firm* — Ladas & Parry LLP

(57) ABSTRACT

The present invention relates to antibodies that bind human programmed cell death 1 (PD-1), and may be useful for treating cancer alone and in combination with chemotherapy and other cancer therapeutics.

31 Claims, No Drawings
Specification includes a Sequence Listing.

SEQUENCE LISTING

<160> NUMBER OF SEQ ID NOS: 30

<210> SEQ ID NO 1
<211> LENGTH: 288
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly

```
                         245                 250                 255
Met Gly Thr Ser Ser Pro Ala Arg Arg Gly Ser Ala Asp Gly Pro Arg
                 260                 265                 270
Ser Ala Gln Pro Leu Arg Pro Glu Asp Gly His Cys Ser Trp Pro Leu
         275                 280                 285
```

<210> SEQ ID NO 2
<211> LENGTH: 13
<212> TYPE: PRT
<213> ORGANISM: Artificial Sequence
<220> FEATURE:
<223> OTHER INFORMATION: Synthetic Construct

<400> SEQUENCE: 2

```
Lys Ala Ser Gly Gly Thr Phe Ser Ser Tyr Ala Ile Ser
1               5                   10
```

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

```
Lys Ala Ser Gly Gly Thr Leu Ser Ser Tyr Ala Ile Ser
1               5                   10
```

<210> SEQ ID NO 4
<211> LENGTH: 17
<212> TYPE: PRT
<213> ORGANISM: Artificial Sequence
<220> FEATURE:
<223> OTHER INFORMATION: Synthetic Construct

<400> SEQUENCE: 4

```
Leu Ile Ile Pro Met Phe Gly Thr Ala Gly Tyr Ala Gln Lys Phe Gln
1               5                   10                  15

Gly
```

<210> SEQ ID NO 5
<211> LENGTH: 17
<212> TYPE: PRT
<213> ORGANISM: Artificial Sequence
<220> FEATURE:
<223> OTHER INFORMATION: Synthetic Construct

<400> SEQUENCE: 5

```
Leu Ile Ile Pro Met Phe Asp Thr Ala Gly Tyr Ala Gln Lys Phe Gln
1               5                   10                  15

Gly
```

<210> SEQ ID NO 6
<211> LENGTH: 17
<212> TYPE: PRT
<213> ORGANISM: Artificial Sequence
<220> FEATURE:
<223> OTHER INFORMATION: Synthetic Construct

<400> SEQUENCE: 6

```
Leu Ile Ile Pro Met Phe Gly Ala Ala Gly Tyr Ala Gln Arg Phe Gln
1               5                   10                  15

Gly
```

<210> SEQ ID NO 7
<211> LENGTH: 13
<212> TYPE: PRT
<213> ORGANISM: Artificial Sequence
<220> FEATURE:
<223> OTHER INFORMATION: Synthetic Construct

<400> SEQUENCE: 7

Ala Arg Ala Glu Tyr Ser Ser Thr Gly Thr Phe Asp Tyr
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic Construct

<400> SEQUENCE: 8

Ala Arg Ala Glu His Ser Ser Thr Gly Thr Phe Asp Tyr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic Construct

<400> SEQUENCE: 9

Arg Ala Ser Gln Gly Ile Ser Ser Trp Leu Ala
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Ser Ala Ala Ser Ser Leu Gln Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Gln Gln Ala Asn His Leu Pro Phe Thr
1               5

<210> SEQ ID NO 12
<211> LENGTH: 120
<212> TYPE: PRT
<213> ORGANISM: Artificial Sequence
<220> FEATURE:
<223> OTHER INFORMATION: Synthetic Construct

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr

```
            20                  25                  30
Ala Ile Ser Trp Val Arg Gln Ala Pro Gly Gln Gly Leu Glu Trp Met
            35                  40                  45

Gly Leu Ile Ile Pro Met Phe Gly Thr Ala Gly Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ala Glu Tyr Ser Ser Thr Gly Thr Phe Asp Tyr Trp Gly Gln
            100                 105                 110

Gly Thr Leu Val Thr Val Ser Ser
            115                 120

<210> SEQ ID NO 13
<211> LENGTH: 120
<212> TYPE: PRT
<213> ORGANISM: Artificial Sequence
<220> FEATURE:
<223> OTHER INFORMATION: Synthetic Construct

<400> SEQUENCE: 13

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Leu Ile Ile Pro Met Phe Asp Thr Ala Gly Tyr Ala Gln Lys Phe
        50                  55                  60

Gln Gly Arg Val Ala Ile Thr Val Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
            100                 105                 110

Gly Thr Leu Val Thr Val Ser Ser
            115                 120

<210> SEQ ID NO 14
<211> LENGTH: 120
<212> TYPE: PRT
<213> ORGANISM: Artificial Sequence
<220> FEATURE:
<223> OTHER INFORMATION: Synthetic Construct

<400> SEQUENCE: 14

Gln Val Gln Leu Val Gln Ser Gly Ala Glu Val Lys Lys Pro Gly Ser
 1               5                  10                  15

Ser Val Arg Val Ser Cys Lys Ala Ser Gly Gly Thr Leu Ser Ser Tyr
            20                  25                  30

Ala Ile Ser Trp Val Arg Gln Ala Pro Gly Gln Gly Leu Glu Trp Met
            35                  40                  45

Gly Leu Ile Ile Pro Met Phe Gly Ala Ala Gly Tyr Ala Gln Arg Phe
        50                  55                  60

Gln Gly Arg Val Thr Ile Thr Ala Asp Glu Ser Ala Ser Thr Ala Tyr
 65                  70                  75                  80
```

```
Met Glu Leu Ser Ser Leu Arg Ser Glu Asp Thr Ala Val Tyr Tyr Cys
                 85                  90                  95

Ala Arg Ala Glu His Ser Ser Thr Gly Thr Phe Asp Tyr Trp Gly Gln
            100                 105                 110

Gly Thr Leu Val Thr Val Ser Ser
        115                 120

<210> SEQ ID NO 15
<211> LENGTH: 107
<212> TYPE: PRT
<213> ORGANISM: Artificial Sequence
<220> FEATURE:
<223> OTHER INFORMATION: Synthetic Construct

<400> SEQUENCE: 15

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn His Leu Pro Phe
                85                  90                  95

Thr Phe Gly Gly Gly Thr Lys Val Glu Ile Lys
            100                 105

<210> SEQ ID NO 16
<211> LENGTH: 447
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Leu Ile Ile Pro Met Phe Gly Thr Ala Gly Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu Tyr Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
        435                 440                 445

<210> SEQ ID NO 17
<211> LENGTH: 447
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Leu Ile Ile Pro Met Phe Asp Thr Ala Gly Tyr Ala Gln Lys Phe
    50                  55                  60
Gln Gly Arg Val Ala Ile Thr Val Asp Glu Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 18
<211> LENGTH: 447
<212> TYPE: PRT
<213> ORGANISM: Artificial Sequence
<220> FEATURE:
<223> OTHER INFORMATION: Synthetic Construct

<400> SEQUENCE: 18

```
Gln Val Gln Leu Val Gln Ser Gly Ala Glu Val Lys Pro Gly Ser
  1               5                  10                  15

Ser Val Arg Val Ser Cys Lys Ala Ser Gly Gly Thr Leu Ser Ser Tyr
            20                  25                  30

Ala Ile Ser Trp Val Arg Gln Ala Pro Gly Gln Gly Leu Glu Trp Met
        35                  40                  45

Gly Leu Ile Ile Pro Met Phe Gly Ala Ala Gly Tyr Ala Gln Arg Phe
    50                  55                  60

Gln Gly Arg Val Thr Ile Thr Ala Asp Glu Ser Ala Ser Thr Ala Tyr
 65              70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Arg Leu Thr Val Asp Lys Ser Arg
                405                 410                 415
```

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 19
<211> LENGTH: 446
<212> TYPE: PRT
<213> ORGANISM: Artificial Sequence
<220> FEATURE:
<223> OTHER INFORMATION: Synthetic Construct

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Leu Ile Ile Pro Met Phe Gly Thr Ala Gly Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu Tyr Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
            435                 440                 445

<210> SEQ ID NO 20
<211> LENGTH: 446
<212> TYPE: PRT
<213> ORGANISM: Artificial Sequence
<220> FEATURE:
<223> OTHER INFORMATION: Synthetic Construct

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Leu Ile Ile Pro Met Phe Asp Thr Ala Gly Tyr Ala Gln Lys Phe
    50                  55                  60

Gln Gly Arg Val Ala Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ala Glu His Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
            245                 250                 255

-continued

```
Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 21
<211> LENGTH: 446
<212> TYPE: PRT
<213> ORGANISM: Artificial Sequence
<220> FEATURE:
<223> OTHER INFORMATION: Synthetic Construct

<400> SEQUENCE: 21

Gln Val Gln Leu Val Gln Ser Gly Ala Glu Val Lys Lys Pro Gly Ser
1               5                   10                  15

Ser Val Arg Val Ser Cys Lys Ala Ser Gly Thr Leu Ser Ser Tyr
            20                  25                  30

Ala Ile Ser Trp Val Arg Gln Ala Pro Gly Gln Gly Leu Glu Trp Met
        35                  40                  45

Gly Leu Ile Ile Pro Met Phe Gly Ala Ala Gly Tyr Ala Gln Arg Phe
    50                  55                  60

Gln Gly Arg Val Thr Ile Thr Ala Asp Glu Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 22
<211> LENGTH: 214
<212> TYPE: PRT
<213> ORGANISM: Artificial Sequence
<220> FEATURE:
<223> OTHER INFORMATION: Synthetic Construct

<400> SEQUENCE: 22

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn His Leu Pro Phe
                85                  90                  95
```

```
Thr Phe Gly Gly Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
            210

<210> SEQ ID NO 23
<211> LENGTH: 447
<212> TYPE: PRT
<213> ORGANISM: Artificial Sequence
<220> FEATURE:
<223> OTHER INFORMATION: Synthetic Construct

<400> SEQUENCE: 23

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
                20                  25                  30
Ala Ile Ser Trp Val Arg Gln Ala Pro Gly Gln Gly Leu Glu Trp Met
            35                  40                  45
Gly Leu Ile Ile Pro Met Phe Gly Thr Ala Gly Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ala Glu Tyr Ser Ser Thr Gly Thr Phe Asp Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
210                 215                 220
Pro Cys Pro Ser Cys Pro Ala Pro Glu Phe Leu Gly Gly Pro Ser Val
225                 230                 235                 240
```

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 24
<211> LENGTH: 447
<212> TYPE: PRT
<213> ORGANISM: Artificial Sequence
<220> FEATURE:
<223> OTHER INFORMATION: Synthetic Construct

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Leu Ile Ile Pro Met Phe Asp Thr Ala Gly Tyr Ala Gln Lys Phe
    50                  55                  60

Gln Gly Arg Val Ala Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

```
Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 25
<211> LENGTH: 447
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Leu Ser Ser Tyr
            20                  25                  30

Ala Ile Ser Trp Val Arg Gln Ala Pro Gly Gln Gly Leu Glu Trp Met
        35                  40                  45

Gly Leu Ile Ile Pro Met Phe Gly Ala Ala Gly Tyr Ala Gln Arg Phe
    50                  55                  60

Gln Gly Arg Val Thr Ile Thr Ala Asp Glu Ser Ala Ser Thr Ala Tyr
65                  70                  75                  80
```

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 26
<211> LENGTH: 1347
<212> TYPE: DNA
<213> ORGANISM: Artificial Sequence
<220> FEATURE:
<223> OTHER INFORMATION: Synthetic Construct

<400> SEQUENCE: 26

| | |
|---|---|
| caggtgcagc tggtgcagag cggcgctgag gtgaagaagc ctggctccag cgtgaaggtg | 60 |
| tcctgcaaag cctccggcgg caccttcagc tcctacgcta tcagctgggt gaggcaggct | 120 |
| cctggccagg gactggagtg gatgggcctg atcatcccca tgttcggcac cgctggctac | 180 |
| gcccagaagt tccagggcag ggtgaccatc accgccacg agtccacctc caccgcctac | 240 |
| atggagctgt cctccctgag gtccgaggac accgccgtgt actactgtgc cagggccgag | 300 |
| tactcctcca ccggcacctt cgactactgg ggccagggca cactcgtgac cgtcagctcc | 360 |
| gccagcacaa agggcccag cgtgtttccc ctggcccctt gcagcaggag cacatccgag | 420 |
| agcaccgctg ccctgggatg tctggtgaag gactatttcc ccgagcccgt gacagtgagc | 480 |
| tggaacagcg gagccctgac ctccggagtg cacaccttcc ctgccgtgct gcagagcagc | 540 |
| ggactgtaca gcctgtccag cgtggtgaca gtgccttcct ccagcctcgg cacaaagacc | 600 |
| tacacctgca acgtggacca caagccctcc aacaccaaag tggacaagcg ggtggaaagc | 660 |
| aagtatggac ccccttgccc tccttgtccc gcccctgagt tcctgggagg cccttccgtc | 720 |
| ttcctgtttc cccccaagcc caaggacaca ctcatgattt ccaggacccc cgaggtgacc | 780 |
| tgcgtcgtgg tcgacgtgag ccaggaggac cccgaggtgc agtttaactg gtatgtggac | 840 |
| ggcgtggagg tccacaatgc caaaaccaag cccagggagg aacagttcaa ctccacctat | 900 |
| agggtggtca gcgtgctgac cgtcctgcac caggactggc tgaacggaaa ggagtataag | 960 |
| tgcaaagtct ccaacaaggg cctgcctagc agcatcgaga gaccatctc caaagccaag | 1020 |
| ggccagccca gggagcccca ggtttatact ctgccccctt cccaggagga tgaccaag | 1080 |
| aatcaggtgt ccctgacctg cctggtgaaa ggcttttacc cctccgacat cgctgtggag | 1140 |
| tgggagagca atggccagcc cgagaacaac tacaagacca ccccccccgt gctggatagc | 1200 |
| gatggcagct tcttcctcta cagcaggctg accgtggata gagcaggtg gcaggagggc | 1260 |
| aacgtgtttt cctgctccgt gatgcatgag gccctccaca accattacac acagaaaagc | 1320 |
| ctgagcctga gcctgggcaa gtgatga | 1347 |

<210> SEQ ID NO 27
<211> LENGTH: 1347
<212> TYPE: DNA
<213> ORGANISM: Artificial Sequence
<220> FEATURE:
<223> OTHER INFORMATION: Synthetic Construct

<400> SEQUENCE: 27

| | |
|---|---|
| caagtgcagc tggtgcagtc cggcgctgag gtgaaaaaac ccggatcctc cgtcaaggtg | 60 |
| tcctgtaaag ccagcggcgg cacattcagc agctacgcca tctcctgggt gaggcaagct | 120 |
| cctggacagg gctggaatg gatgggcctg atcatcccca tgttcgacac cgccggctac | 180 |
| gctcagaaat tccagggccg ggtcgccatt acagtggatg agagcaccag cacagcctac | 240 |
| atggagctca gctccctgag gagcgaagat accgccgtct actattgtgc ccgggctgag | 300 |
| catagcagca ccggcacctt cgactattgg ggccagggaa ccctggtcac agtgagctcc | 360 |
| gcttccacaa agggcccag cgtgtttccc ctggcccctt gtagcaggtc cacctccgaa | 420 |
| agcacagccg ctctggcctg cctggtcaag gattacttcc ccgagcccgt gaccgtgtcc | 480 |
| tggaatagcg gcgctctcac atccggagtg cataccttc tgccgtgct ccagtcctcc | 540 |
| ggcctgtact ccctgagctc cgtggtgacc gtcccttcca gctccctggg caccaagacc | 600 |
| tatacctgta acgtggacca caagccctcc aataccaagg tggataagcg ggtcgagtcc | 660 |
| aagtacggac ccccttgccc tccttgtcct gctcctgaat tcctcggcgg acctagcgtc | 720 |

```
tttctcttcc ccccaagcc aaggatacc ctgatgatct ccaggacccc cgaggtgaca      780
tgcgtcgtgg tcgatgtgtc ccaggaggat cctgaagtgc agttcaactg gtacgtggac    840
ggcgtcgaag tgcataacgc caagaccaag cccagggagg agcagttcaa ctccacctat    900
cgggtggtga gcgtgctgac cgtgctgcat caggactggc tcaacggcaa agagtacaag    960
tgcaaggtct ccaacaaggg actcccctcc agcatcgaga gaccattag caaggccaaa     1020
ggccaaccca gggagcctca ggtatatacg ctgccccca gccaggagga gatgaccaaa     1080
aaccaggtca gcctcacctg tctggtcaag ggcttctacc ctagcgacat tgctgtcgag    1140
tgggagagca cggccagcc cgagaacaac tataaaacca ccccctgt cctggactcc       1200
gacggatcct tcttcctgta ctccaggctg acagtcgaca agtcccggtg gcaagaggga    1260
aacgtcttct cctgctccgt gatgcacgaa gctctccaca accactacac ccagaagagc    1320
ctcagcctgt ccctgggcaa atgatga                                        1347
```

<210> SEQ ID NO 28
<211> LENGTH: 1347
<212> TYPE: DNA
<213> ORGANISM: Artificial Sequence
<220> FEATURE:
<223> OTHER INFORMATION: Synthetic Construct

<400> SEQUENCE: 28

```
caagtccagc tcgtgcaaag cggagccgag gtgaagaaac ccggcagctc cgtgcgggtg    60
agctgtaagg cctccggagg caccctgtcc agctatgcta tcagctgggt gaggcaggcc    120
cccggacagg gcctggaatg gatgggactg atcatcccta tgtttggagc cgccggctat   180
gctcagaggt tccagggccg ggtcaccatc accgctgacg agagcgccag caccgcctat   240
atggagctgt cctccctgag gagcgaggat accgctgtct actactgtgc cagggccgag   300
cactcctcca caggaaccctt cgactactgg ggcagggca ccctggtgac agtgtcctcc    360
gcctccacca agggcccttc cgtgtttcct ctggctcctt gctcccggtc caccagcgag    420
tccacagccg ctctgggctg tctggtgaag gactatttcc ccgagcctgt gaccgtcagc    480
tggaatagcg gcgccctgac ctccggagtg cacacattcc ccgccgtcct gcagagcagc    540
ggactctact ccctgagctc cgtggtgacc gtgccttcca gcagcctggg aaccaagacc    600
tacacctgca tgtgaccca caaacccagc aacaccaagg tggataagcg ggtggaatcc    660
aagtacggcc ctccctgtcc cccttgtccc gctcccgaat tcctgggcgg acctagcgtg    720
ttcctgtttc ccctaagcc caaggatacc ctgatgatct ccaggacccc gaagtcacc     780
tgcgtcgtcg tggacgtgtc ccaggaggac cctgaagtcc agtttaattg gtacgtcgac    840
ggcgtggagg tgcacaacgc caagacaaag cctcggagg agcagttcaa cagccactac    900
agggtggtga gcgtgctgac cgtgctgcac caggactggc tgaacggcaa agagtacaag    960
tgcaaggtga gcaacaaggg cctgcctcc tccatcgaga gaccatctc caaggccaaa     1020
ggccagccga gggagccca ggtgtacacc ctgccccta gccaggagga gatgaccaag     1080
aaccaggtct ccctgacctg cctggtgaag ggattctatc ccagcgacat tgccgtggag    1140
tgggagtcca cggccagcc cgagaataac tacaagacca ccccctgt gctggacagc      1200
gacgggagct tcttcctgta ttccggctg accgtcgaca agtcccggtg gcaggagggc    1260
aacgtgttta gctgcagcgt gatgcacgaa gccctccaca accactatac ccagaagagc    1320
ctgtccctgt ccctgggcaa gtgatga                                        1347
```

<210> SEQ ID NO 29
<211> LENGTH: 1338
<212> TYPE: DNA
<213> ORGANISM: Artificial Sequence
<220> FEATURE:
<223> OTHER INFORMATION: Synthetic Construct

<400> SEQUENCE: 29

```
caggtgcagc tggtccagtc aggggctgaa gtgaagaagc ccggcagctc cgtgaaggtg      60
tcttgcaagg ccagcggcgg aacattctcc agttacgcca tctcttgggt gcggcaggct     120
ccaggccagg gcctggagtg gatgggcctg atcatcccca tgttcgacac cgccgggtat     180
gcccagaagt tcagggcag agtggcaatc acagtggacg agagcacctc cacagcctac     240
atggagctgt ctagcctgag atccgaggat accgccgtgt attattgtgc ccgggccgaa     300
cacagctcta cagggacttt cgactactgg ggccagggca ccctggtgac agtgtcctct     360
gctagcacca agggcccatc ggtcttcccg ctcgcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacctgca acgtagatca caagcccagc aacaccaagg tggacaagag agttgagtcc     660
aaatatggtc ccccatgccc acctgccca gcacctgagg ccgccggggg accatcagtc     720
ttcctgttcc ccccaaaacc caaggacact ctcatgatct cccggacccc tgaggtcacg     780
tgcgtggtgg tggacgtgag ccaggaagac cccgaggtcc agttcaactg gtatgttgat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtct ccaacaaagg cctcccgtcc tccatcgaga aaaccatctc caaagccaaa    1020
gggcagcccc gagagccaca ggtgtacacc ctgcccccat cccaagaaga atgaccaaa    1080
aaccaagtca gcctgacctg cctggtcaaa ggcttctacc ccagcgacat cgccgtggag    1140
tgggaaagca atgggcagcc ggagaacaac tacaagacca cgcctcccgt gctggactcc    1200
gacggctcct tcttcctcta ctcccgtcta accgtggaca agagcaggtg gcaggagggg    1260
aatgtcttct catgctccgt gatgcatgag gctctgcaca accactacac acagaagagc    1320
ctctcccctgt ctctgggt                                                 1338
```

<210> SEQ ID NO 30
<211> LENGTH: 648
<212> TYPE: DNA
<213> ORGANISM: Artificial Sequence
<220> FEATURE:
<223> OTHER INFORMATION: Synthetic Construct

<400> SEQUENCE: 30

```
gacatccaga tgacacagtc ccctagctcc gtgtccgctt ccgtgggaga cagggtgaca      60
atcacatgca gggcttccca gggcatcagc agctggctgg cttggtatca gcagaagccc     120
ggcaaggccc ccaagctgct gatcagcgct gctagctccc tgcagtccgg agtgccttcc     180
aggttctccg gctccggaag cggcaccgac ttcaccctga ccatctccag cctgcagccc     240
gaggacttcg ccacctacta ctgccaacag gccaaccacc tgcccttcac cttcggcggc     300
ggcaccaagg tggagatcaa gaggaccgtg gccgccccct ccgtgttcat ctttccccc     360
agcgacgagc agctgaagag cggcaccgcc tccgtggtgt gcctgctgaa caacttctat     420
```

```
ccccgggagg ccaaggtgca gtggaaggtc gacaatgccc tgcagagcgg caactcccag    480
gagagcgtga ccgagcagga cagcaaggac tccacctact ccctgagctc caccctgaca    540
ctgtccaagg ccgactacga gaagcacaag gtgtacgcct gcgaggtgac acaccagggc    600
ctgagctccc ccgtgaccaa gtccttcaac aggggcgagt gctgatga                648
```

PD-1 ANTIBODIES

The present invention relates to the field of medicine. More particularly, the present invention relates to antibodies that bind human programmed cell death 1 (PD-1), and may be useful for treating cancer alone and in combination with chemotherapy and other cancer therapeutics.

Tumor cells escape detection and elimination by the immune system through multiple mechanisms. Immune checkpoint pathways are used in self-tolerance maintenance and activated T cell control, but cancer cells can use the pathways to prevent destruction. The PD-1/human programmed cell death 1 ligand 1 (PD-L1) pathway is one such immune checkpoint. Human PD-1 is found on T cells, and the binding of PD-L1 and human programmed cell death 1 ligand 2 (PD-L2) to PD-1 inhibits T cell proliferation and cytokine production. Tumor cell production of PD-L1 and PD-L2 can therefore allow escape from T cell surveillance.

A fully human IgG4 (S228P) antibody against human PD-1, nivolumab, has been shown to inhibit the binding of PD-1 to PD-L1 and PD-L2, and has been tested in various clinical trials. (Wang et al., Cancer Immunol Res (2014) 2(9):846). A humanized IgG4 (S228P) antibody against PD-1, pembrolizumab (formerly lambrolizumab), has been shown to inhibit the binding of PD-1 to PD-L1 and PD-L2, and has been tested in various clinical trials. (WO2008156712 and Hamid et al., N Engl J Med (2013) 369:2).

There remains a need to provide alternative antibodies that bind and neutralize human PD-1 interaction with PD-L1 and PD-L2. In particular, there remains a need to provide antibodies that bind human PD-1 with higher affinity than certain prior art antibodies. Also, there remains a need to provide antibodies that more effectively block the human PD-1 interaction with PD-L1 and PD-L2 than certain prior art antibodies. Higher affinity and better blocking, alone or together, can translate into greater in vivo activity or lower required dosing amounts.

Certain antibodies of the present invention bind human PD-1 with higher affinity than nivolumab and pembrolizumab. Furthermore, certain antibodies of the present invention mediate preferential enhanced alloreactivity compared to nivolumab and pembrolizumab in an in vivo model.

Accordingly, in some embodiments the present invention provides an antibody that binds human PD-1 (SEQ ID NO: 1), comprising a light chain (LC) and a heavy chain (HC), wherein the light chain comprises light chain complementarity determining regions LCDR1, LCDR2, and LCDR3 consisting of the amino acid sequences RASQGISSWLA (SEQ ID NO: 9), SAASSLQS (SEQ ID NO: 10), and QQANHLPFT (SEQ ID NO: 11), respectively, and wherein the heavy chain comprises heavy chain complementarity determining regions HCDR1, HCDR2, and HCDR3, wherein HCDR1 consists of the amino acid sequences KASGGTFSSYAIS (SEQ ID NO: 2) or KASGGTLSSYAIS (SEQ ID NO: 3), wherein HCDR2 consists of the amino acid sequences LIIPMFGTAGYAQKFQG (SEQ ID NO: 4), LIIPMFDTAGYAQKFQG (SEQ ID NO: 5) or LIIPMFGAAGYAQRFQG (SEQ ID NO: 6), and wherein HCDR3 consists of the amino acid sequences ARAEYSSTGTFDY (SEQ ID NO: 7) or ARAEHSSTGTFDY (SEQ ID NO: 8).

In some embodiments, the present invention provides an antibody, wherein LCDR1, LCDR2, and LCDR3 consist of the amino acid sequences RASQGISSWLA (SEQ ID NO: 9), SAASSLQS (SEQ ID NO: 10), and QQANHLPFT (SEQ ID NO: 11), respectively, and wherein HCDR1, HCDR2, and HCDR3 consist of the amino acid sequences KASGGTFSSYAIS (SEQ ID NO: 2), LIIPMFGTAGYAQKFQG (SEQ ID NO: 4), and ARAEYSSTGTFDY (SEQ ID NO: 7), respectively.

In some embodiments, the present invention provides an antibody, wherein LCDR1, LCDR2, and LCDR3 consist of the amino acid sequences RASQGISSWLA (SEQ ID NO: 9), SAASSLQS (SEQ ID NO: 10), and QQANHLPFT (SEQ ID NO: 11), respectively, and wherein HCDR1, HCDR2, and HCDR3 consist of the amino acid sequences KASGGTFSSYAIS (SEQ ID NO: 2), LIIPMFDTAGYAQKFQG (SEQ ID NO: 5), and ARAEHSSTGTFDY (SEQ ID NO: 8), respectively.

In some embodiments, the present invention provides an antibody, wherein LCDR1, LCDR2, and LCDR3 consist of the amino acid sequences RASQGISSWLA (SEQ ID NO: 9), SAASSLQS (SEQ ID NO: 10), and QQANHLPFT (SEQ ID NO: 11), respectively, and wherein HCDR1, HCDR2, and HCDR3 consist of the amino acid sequences KASGGTLSSYAIS (SEQ ID NO: 3), LIIPMFGAAGYAQRFQG (SEQ ID NO: 6), and ARAEHSSTGTFDY (SEQ ID NO: 8), respectively.

In some embodiments, the present invention provides an antibody, comprising a light chain (LC) and a heavy chain (HC), wherein the light chain comprises a light chain variable region (LCVR) and the heavy chain comprises a heavy chain variable region (HCVR), wherein the LCVR has the amino acid sequence given in SEQ ID NO: 15, and the HCVR has the amino acid sequence given in SEQ ID NO: 12, SEQ ID NO: 13, or SEQ ID NO: 14.

In further embodiments, the present invention provides an antibody, wherein the LCVR has the amino acid sequence given in SEQ ID NO: 15, and the HCVR has the amino acid sequence given in SEQ ID NO: 12. In further embodiments, the present invention provides an antibody, wherein the LCVR has the amino acid sequence given in SEQ ID NO: 15, and the HCVR has the amino acid sequence given in SEQ ID NO: 13. In further embodiments, the present invention provides an antibody, wherein the LCVR has the amino acid sequence given in SEQ ID NO: 15, and the HCVR has the amino acid sequence given in SEQ ID NO: 14.

In some embodiments, the present invention provides an antibody, wherein the LC has the amino acid sequence given in SEQ ID NO: 22, and the HC has the amino acid sequence given in SEQ ID NO: 16, SEQ ID NO: 17, SEQ ID NO: 18, SEQ ID NO: 19, SEQ ID NO: 20, or SEQ ID NO: 21.

In a further embodiment, the present invention provides an antibody, wherein the LC has the amino acid sequence given in SEQ ID NO: 22, and the HC has the amino acid sequence given in SEQ ID NO: 16. In a further embodiment, the present invention provides an antibody, wherein the LC has the amino acid sequence given in SEQ ID NO: 22, and the HC has the amino acid sequence given in SEQ ID NO: 17. In a further embodiment, the present invention provides an antibody, wherein the LC has the amino acid sequence given in SEQ ID NO: 22, and the HC has the amino acid sequence given in SEQ ID NO: 18. In a further embodiment, the present invention provides an antibody, wherein the LC has the amino acid sequence given in SEQ ID NO: 22, and the HC has the amino acid sequence given in SEQ ID NO: 19. In a further embodiment, the present invention provides an antibody, wherein the LC has the amino acid sequence given in SEQ ID NO: 22, and the HC has the amino acid sequence given in SEQ ID NO: 20. In a further embodiment, the present invention provides an antibody, wherein the LC has the amino acid sequence given in SEQ ID NO: 22, and the HC has the amino acid sequence given in SEQ ID NO: 21.

In an embodiment, the present invention provides an antibody, wherein the LC has the amino acid sequence given in SEQ ID NO: 22, and the HC has the amino acid sequence given in SEQ ID NO: 23. In an embodiment, the present invention provides an antibody, wherein the LC has the amino acid sequence given in SEQ ID NO: 22, and the HC has the amino acid sequence given in SEQ ID NO: 24. In an embodiment, the present invention provides an antibody, wherein the LC has the amino acid sequence given in SEQ ID NO: 22, and the HC has the amino acid sequence given in SEQ ID NO: 25.

In an embodiment, the present invention provides an antibody, comprising two light chains and two heavy chains, wherein each light chain has the amino acid sequence given in SEQ ID NO: 22, and each heavy chain has the amino acid sequence given in SEQ ID NO: 16, SEQ ID NO: 17, SEQ ID NO: 18, SEQ ID NO: 19, SEQ ID NO: 20, or SEQ ID NO: 21.

In a further embodiment, the present invention provides an antibody, wherein each light chain has the amino acid sequence given in SEQ ID NO: 22, and each heavy chain has the amino acid sequence given in SEQ ID NO: 16. In a further embodiment, the present invention provides an antibody, wherein each light chain has the amino acid sequence given in SEQ ID NO: 22, and each heavy chain has the amino acid sequence given in SEQ ID NO: 17. In a further embodiment, the present invention provides an antibody, wherein each light chain has the amino acid sequence given in SEQ ID NO: 22, and each heavy chain has the amino acid sequence given in SEQ ID NO: 18. In a further embodiment, the present invention provides an antibody, wherein each light chain has the amino acid sequence given in SEQ ID NO: 22, and each heavy chain has the amino acid sequence given in SEQ ID NO: 19. In a further embodiment, the present invention provides an antibody, wherein each light chain has the amino acid sequence given in SEQ ID NO: 22, and each heavy chain has the amino acid sequence given in SEQ ID NO: 20. In a further embodiment, the present invention provides an antibody, wherein each light chain has the amino acid sequence given in SEQ ID NO: 22, and each heavy chain has the amino acid sequence given in SEQ ID NO: 21.

In an embodiment, the present invention provides an antibody, comprising two light chains and two heavy chains, wherein each light chain has the amino acid sequence given in SEQ ID NO: 22, and each heavy chain has the amino acid sequence given in SEQ ID NO: 23. In an embodiment, the present invention provides an antibody, comprising two light chains and two heavy chains, wherein each light chain has the amino acid sequence given in SEQ ID NO: 22, and each heavy chain has the amino acid sequence given in SEQ ID NO: 24. In an embodiment, the present invention provides an antibody, comprising two light chains and two heavy chains, wherein each light chain has the amino acid sequence given in SEQ ID NO: 22, and each heavy chain has the amino acid sequence given in SEQ ID NO: 25.

In an embodiment, the present invention provides an antibody, wherein one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain. In an embodiment, the present invention provides an antibody, wherein the antibody is glycosylated.

In an embodiment, the present invention provides an antibody that binds human PD-1 (SEQ ID NO: 1), comprising a light chain (LC) and a heavy chain (HC), wherein the light chain comprises a light chain variable region (LCVR) and the heavy chain comprises a heavy chain variable region (HCVR), wherein the LCVR has the amino acid sequence given in SEQ ID NO: 15, and the HCVR has the amino acid sequence given in SEQ ID NO: 12, SEQ ID NO: 13, or SEQ ID NO: 14.

In a further embodiment, the present invention provides an antibody that binds human PD-1 (SEQ ID NO: 1), wherein the LCVR has the amino acid sequence given in SEQ ID NO: 15, and the HCVR has the amino acid sequence given in SEQ ID NO: 12. In a further embodiment, the present invention provides an antibody that binds human PD-1 (SEQ ID NO: 1), wherein the LCVR has the amino acid sequence given in SEQ ID NO: 15, and the HCVR has the amino acid sequence given in SEQ ID NO: 13. In a further embodiment, the present invention provides an antibody that binds human PD-1 (SEQ ID NO: 1), wherein the LCVR has the amino acid sequence given in SEQ ID NO: 15, and the HCVR has the amino acid sequence given in SEQ ID NO: 14.

In an embodiment, the present invention provides an antibody that binds human PD-1 (SEQ ID NO: 1), wherein the LC has the amino acid sequence given in SEQ ID NO: 22, and the HC has the amino acid sequence given in SEQ ID NO: 16, SEQ ID NO: 17, SEQ ID NO: 18, SEQ ID NO: 19, SEQ ID NO: 20, or SEQ ID NO: 21.

In a further embodiment, the present invention provides an antibody that binds human PD-1 (SEQ ID NO: 1), wherein the LC has the amino acid sequence given in SEQ ID NO: 22, and the HC has the amino acid sequence given in SEQ ID NO: 16. In a further embodiment, the present invention provides an antibody that binds human PD-1 (SEQ ID NO: 1), wherein the LC has the amino acid sequence given in SEQ ID NO: 22, and the HC has the amino acid sequence given in SEQ ID NO: 17. In a further embodiment, the present invention provides an antibody that binds human PD-1 (SEQ ID NO: 1), wherein the LC has the amino acid sequence given in SEQ ID NO: 22, and the HC has the amino acid sequence given in SEQ ID NO: 18. In a further embodiment, the present invention provides an antibody that binds human PD-1 (SEQ ID NO: 1), wherein the LC has the amino acid sequence given in SEQ ID NO: 22, and the HC has the amino acid sequence given in SEQ ID NO: 19. In a further embodiment, the present invention provides an antibody that binds human PD-1 (SEQ ID NO: 1), wherein the LC has the amino acid sequence given in SEQ ID NO: 22, and the HC has the amino acid sequence given in SEQ ID NO: 20. In a further embodiment, the present invention provides an antibody that binds human PD-1 (SEQ ID NO: 1), wherein the LC has the amino acid sequence given in SEQ ID NO: 22, and the HC has the amino acid sequence given in SEQ ID NO: 21.

In an embodiment, the present invention provides an antibody that binds human PD-1 (SEQ ID NO: 1), wherein the LC has the amino acid sequence given in SEQ ID NO: 22, and the HC has the amino acid sequence given in SEQ ID NO: 23. In an embodiment, the present invention provides an antibody that binds human PD-1 (SEQ ID NO: 1), wherein the LC has the amino acid sequence given in SEQ ID NO: 22, and the HC has the amino acid sequence given in SEQ ID NO: 24. In an embodiment, the present invention provides an antibody that binds human PD-1 (SEQ ID NO:

1), wherein the LC has the amino acid sequence given in SEQ ID NO: 22, and the HC has the amino acid sequence given in SEQ ID NO: 25.

In an embodiment, the present invention provides an antibody that binds human PD-1 (SEQ ID NO: 1), comprising two light chains and two heavy chains, wherein each light chain has the amino acid sequence given in SEQ ID NO: 22, and each heavy chain has the amino acid sequence given in SEQ ID NO: 16, SEQ ID NO: 17, SEQ ID NO: 18, SEQ ID NO: 19, SEQ ID NO: 20, or SEQ ID NO: 21.

In a further embodiment, the present invention provides an antibody that binds human PD-1 (SEQ ID NO: 1), wherein each light chain has the amino acid sequence given in SEQ ID NO: 22, and each heavy chain has the amino acid sequence given in SEQ ID NO: 16. In a further embodiment, the present invention provides an antibody that binds human PD-1 (SEQ ID NO: 1), wherein each light chain has the amino acid sequence given in SEQ ID NO: 22, and each heavy chain has the amino acid sequence given in SEQ ID NO: 17. In a further embodiment, the present invention provides an antibody that binds human PD-1 (SEQ ID NO: 1), wherein each light chain has the amino acid sequence given in SEQ ID NO: 22, and each heavy chain has the amino acid sequence given in SEQ ID NO: 18. In a further embodiment, the present invention provides an antibody that binds human PD-1 (SEQ ID NO: 1), wherein each light chain has the amino acid sequence given in SEQ ID NO: 22, and each heavy chain has the amino acid sequence given in SEQ ID NO: 19. In a further embodiment, the present invention provides an antibody that binds human PD-1 (SEQ ID NO: 1), wherein each light chain has the amino acid sequence given in SEQ ID NO: 22, and each heavy chain has the amino acid sequence given in SEQ ID NO: 20. In a further embodiment, the present invention provides an antibody that binds human PD-1 (SEQ ID NO: 1), wherein each light chain has the amino acid sequence given in SEQ ID NO: 22, and each heavy chain has the amino acid sequence given in SEQ ID NO: 21.

In an embodiment, the present invention provides an antibody that binds human PD-1 (SEQ ID NO: 1), comprising two light chains and two heavy chains, wherein each light chain has the amino acid sequence given in SEQ ID NO: 22, and each heavy chain has the amino acid sequence given in SEQ ID NO: 23. In an embodiment, the present invention provides an antibody that binds human PD-1 (SEQ ID NO: 1), comprising two light chains and two heavy chains, wherein each light chain has the amino acid sequence given in SEQ ID NO: 22, and each heavy chain has the amino acid sequence given in SEQ ID NO: 24. In an embodiment, the present invention provides an antibody that binds human PD-1 (SEQ ID NO: 1), comprising two light chains and two heavy chains, wherein each light chain has the amino acid sequence given in SEQ ID NO: 22, and each heavy chain has the amino acid sequence given in SEQ ID NO: 25.

In an embodiment, the present invention provides an antibody that binds human PD-1 (SEQ ID NO: 1), wherein one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain.

In an embodiment, the present invention provides an antibody that binds human PD-1 (SEQ ID NO: 1), wherein the antibody is glycosylated.

In an embodiment, the present invention provides a mammalian cell, comprising a DNA molecule comprising a polynucleotide sequence encoding a polypeptide having an amino acid sequence of SEQ ID NO: 22 and a polynucleotide sequence encoding a polypeptide having an amino acid sequence of SEQ ID NO: 16 or SEQ ID NO: 19, wherein the cell is capable of expressing an antibody comprising a light chain having an amino acid sequence of SEQ ID NO: 22 and a heavy chain having an amino acid sequence of SEQ ID NO: 16 or SEQ ID NO: 19.

In an embodiment, the present invention provides a mammalian cell, comprising a DNA molecule comprising a polynucleotide sequence encoding a polypeptide having an amino acid sequence of SEQ ID NO: 22 and a polynucleotide sequence encoding a polypeptide having an amino acid sequence of SEQ ID NO: 17 or SEQ ID NO: 20, wherein the cell is capable of expressing an antibody comprising a light chain having an amino acid sequence of SEQ ID NO: 22 and a heavy chain having an amino acid sequence of SEQ ID NO: 17 or SEQ ID NO: 20.

In an embodiment, the present invention provides a mammalian cell, comprising a DNA molecule comprising a polynucleotide sequence encoding a polypeptide having an amino acid sequence of SEQ ID NO: 22 and a polynucleotide sequence encoding a polypeptide having an amino acid sequence of SEQ ID NO: 18 or SEQ ID NO: 21, wherein the cell is capable of expressing an antibody comprising a light chain having an amino acid sequence of SEQ ID NO: 22 and a heavy chain having an amino acid sequence of SEQ ID NO: 18 or SEQ ID NO: 21.

In an embodiment, the present invention provides a process for producing an antibody, comprising a light chain having an amino acid sequence of SEQ ID NO: 22 and a heavy chain having an amino acid sequence of SEQ ID NO: 16 or SEQ ID NO: 19, comprising cultivating a mammalian cell of the present invention under conditions such that the antibody is expressed, and recovering the expressed antibody.

In an embodiment, the present invention provides a process for producing an antibody, comprising a light chain having an amino acid sequence of SEQ ID NO: 22 and a heavy chain having an amino acid sequence of SEQ ID NO: 17 or SEQ ID NO: 20, comprising cultivating a mammalian cell of the present invention under conditions such that the antibody is expressed, and recovering the expressed antibody.

In an embodiment, the present invention provides a process for producing an antibody, comprising a light chain having an amino acid sequence of SEQ ID NO: 22 and a heavy chain having an amino acid sequence of SEQ ID NO: 18 or SEQ ID NO: 21, comprising cultivating a mammalian cell of the present invention under conditions such that the antibody is expressed, and recovering the expressed antibody.

In an embodiment, the present invention provides an antibody produced by a process of the present invention.

In an embodiment, the present invention provides a pharmaceutical composition, comprising an antibody of the present invention, and an acceptable carrier, diluent, or excipient.

In an embodiment, the present invention provides a method of treating cancer, comprising administering to a patient in need thereof, an effective amount of an antibody of the present invention. In a further embodiment, the present invention provides a method of treating cancer, comprising administering to a patient in need thereof, an effective amount of an antibody of the present invention, wherein the cancer is melanoma, lung cancer, head and neck cancer, colorectal cancer, pancreatic cancer, gastric cancer, kidney cancer, bladder cancer, prostate cancer, breast cancer, ovarian cancer, or hepatocellular carcinoma.

In a further embodiment, these methods comprise the administration of an effective amount of the antibody of the present invention in simultaneous, separate, or sequential combination with one or more anti-tumor agents. Non-limiting examples of anti-tumor agents include ramucirumab, necitumumab, olaratumab, galunisertib, abemaciclib, cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), and cetuximab.

In a further embodiment, these methods comprise the administration of an effective amount of the compound of the present invention in simultaneous, separate, or sequential combination with one or more immuno-oncology agents. Non-limiting examples of immuno-oncology agents include nivolumab, ipilimumab, pidilizumab, pembrolizumab, tremelimumab, urelumab, lirilumab, atezolizumab, and durvalumab.

In an embodiment, the present invention provides an antibody of the present invention, for use in therapy. In an embodiment, the present invention provides an antibody of the present invention, for use in the treatment of cancer. In a further embodiment, the present invention provides an antibody of the present invention, for use in the treatment of cancer, wherein the cancer is melanoma, lung cancer, head and neck cancer, colorectal cancer, pancreatic cancer, gastric cancer, kidney cancer, bladder cancer, prostate cancer, breast cancer, ovarian cancer, or hepatocellular carcinoma. In a further embodiment, the present invention provides the antibody of the present invention for use in simultaneous, separate, or sequential combination with one or more anti-tumor agents. In a further embodiment, the present invention provides the antibody of the present invention for use in simultaneous, separate, or sequential combination with one or more anti-tumor agents selected from the group consisting of ramucirumab, necitumumab, olaratumab, galunisertib, abemaciclib, cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), and cetuximab, in the treatment of cancer.

In a further embodiment, the present invention provides the antibody of the present invention for use in simultaneous, separate, or sequential combination with one or more immuno-oncology agents. In a further embodiment, the present invention provides the antibody of the present invention for use in simultaneous, separate, or sequential combination with one or more immuno-oncology agents selected from the group consisting of nivolumab, ipilimumab, pidilizumab, pembrolizumab, tremelimumab, urelumab, lirilumab, atezolizumab, and durvalumab, in the treatment of cancer.

In a further embodiment, the present invention provides the use of an antibody of the present invention for the manufacture of a medicament for the treatment of cancer. In a further embodiment, the present invention provides the use of an antibody of the present invention for the manufacture of a medicament for the treatment of cancer, wherein the cancer is melanoma, lung cancer, head and neck cancer, colorectal cancer, pancreatic cancer, gastric cancer, kidney cancer, bladder cancer, prostate cancer, breast cancer, ovarian cancer, or hepatocellular carcinoma.

In a further embodiment, the present invention provides the use of an antibody of the present invention in the manufacture of a medicament for the treatment of cancer wherein said medicament is to be administered simultaneously, separately, or sequentially with one or more anti-tumor agents. In a further embodiment, the present invention provides the use of an antibody of the present invention in the manufacture of a medicament for the treatment of cancer wherein said medicament is to be administered simultaneously, separately, or sequentially with one or more anti-tumor agents selected from the group consisting of ramucirumab, necitumumab, olaratumab, galunisertib, abemaciclib, cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), and cetuximab.

An antibody of the present invention is an engineered, non-naturally occurring polypeptide complex. A DNA molecule of the present invention is a non-naturally occurring DNA molecule that comprises a polynucleotide sequence encoding a polypeptide having the amino acid sequence of one of the polypeptides in an antibody of the present invention.

An antibody of the present invention is designed to have engineered CDRs and have some portions of the antibody (all or parts of the frameworks, hinge regions, and constant regions) to be of human origin that are identical with or substantially identical (substantially human) with frameworks and constant regions derived from human genomic sequences. Fully human frameworks, hinge regions, and constant regions are those human germline sequences as well as sequences with naturally-occurring somatic mutations and those with engineered mutations. An antibody of the present invention may comprise framework, hinge, or constant regions derived from a fully human framework, hinge, or constant region containing one or more amino acid substitutions, deletions, or additions therein. Further, an antibody of the present invention is preferably substantially non-immunogenic in humans.

The antibody of the present invention is an IgG type antibody and has "heavy" chains and "light" chains that are cross-linked via intra- and inter-chain disulfide bonds. Each heavy chain is comprised of an N-terminal HCVR and a heavy chain constant region ("HCCR"). Each light chain is comprised of a LCVR and a light chain constant region ("LCCR"). When expressed in certain biological systems, antibodies having native human Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

Optionally, the antibody of the present invention contains an Fc portion which is derived from human $IgG_4$ Fc region because of a reduced ability to engage Fc receptor-mediated inflammatory mechanisms or to activate complement resulting in reduced effector function.

Certain antibodies of the present invention contain an $IgG_4$-Fc portion that has a serine to proline mutation at position 228. Further, certain antibodies of the present invention contain an $IgG_4$-PAA Fc portion. The $IgG_4$-PAA Fc portion has a serine to proline mutation at position 228, a phenylalanine to alanine mutation at position 234, and a leucine to alanine mutation at position 235. The S228P mutation is a hinge mutation that prevents half-antibody formation (phenomenon of dynamic exchange of half-molecules in IgG$_4$ antibodies). The F234A and L235A mutations further reduce effector function of the already low human IgG$_4$ isotype. Further, certain antibodies of the present invention contain an IgG$_4$-PAA Fc portion with the C-terminal lysine removed (des-Lys) from the heavy chain.

The HCVR and LCVR regions can be further subdivided into regions of hyper-variability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues which form specific interactions with the antigen. There are currently three systems of CDR assignments for antibodies that are used for sequence delineation. The Kabat CDR definition (Kabat et al., "Sequences of Proteins of Immunological Interest," National Institutes of Health, Bethesda, Md. (1991)) is based upon antibody sequence variability. The Chothia CDR definition (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)) is based on three-dimensional structures of antibodies and topologies of the CDR loops. The Chothia CDR definitions are identical to the Kabat CDR definitions with the exception of HCDR1 and HCDR2. The North CDR definition (North et al., "A New Clustering of Antibody CDR Loop Conformations", Journal of Molecular Biology, 406, 228-256 (2011)) is based on affinity propagation clustering with a large number of crystal structures. For the purposes of the present invention, the North CDR definitions are used.

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibody of the present invention may readily be produced in mammalian cells such as CHO, NS0, HEK293 or COS cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host.

Various methods of protein purification may be employed and such methods are known in the art and described, for example, in Deutscher, *Methods in Enzymology* 182: 83-89 (1990) and Scopes, *Protein Purification: Principles and Practice*, 3rd Edition, Springer, N.Y. (1994).

In another embodiment of the present invention, the antibody, or the nucleic acids encoding the same, is provided in isolated form. As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80% (on a molar basis) of the macromolecular species present, preferably more than 90%, and more preferably more than 95%.

The antibody of the present invention, or pharmaceutical compositions comprising the same, may be administered by parenteral routes (e.g., subcutaneous and intravenous). An antibody of the present invention may be administered to a patient alone with pharmaceutically acceptable carriers, diluents, or excipients in single or multiple doses. Pharmaceutical compositions of the present invention can be prepared by methods well known in the art (e.g., *Remington: The Science and Practice of Pharmacy*, 19$^{th}$ ed. (1995), A. Gennaro et al., Mack Publishing Co.) and comprise an antibody, as disclosed herein, and one or more pharmaceutically acceptable carriers, diluents, or excipients.

The term "treating" (or "treat" or "treatment") refers to slowing, interrupting, arresting, alleviating, stopping, reducing, or reversing the progression or severity of an existing symptom, disorder, condition, or disease.

"Binds" as used herein in reference to the affinity of an antibody for human PD-1 is intended to mean, unless indicated otherwise, a $K_D$ of less than about 1×10−6 M, preferably, less than about 1×10−9 M as determined by common methods known in the art, including by use of a surface plasmon resonance (SPR) biosensor at 37° C. essentially as described herein.

For the purposes of the present disclosure, the term "high affinity" refers to a $K_D$ of less than about 150 pM for human PD-1 as determined by MSD or SPR. The $K_D$ values are established by binding kinetics as described in "Binding kinetics and affinity" in the Assays section.

"Effective amount" means the amount of an antibody of the present invention or pharmaceutical composition comprising an antibody of the present invention that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects.

This invention is further illustrated by the following non-limiting example.

EXAMPLE 1

Antibody Expression and Purification

The polypeptides of the variable regions of the heavy chain and light chain, the complete heavy chain and light chain amino acid sequences of Antibody A-Antibody I, and the nucleotide sequences encoding the same, are listed below in the section entitled "Amino Acid and Nucleotide Sequences." In addition, the SEQ ID NOs for the light chain, heavy chain, light chain variable region, and heavy chain variable region of Antibody A-Antibody I are shown in Table 1.

The antibodies of the present invention, including, but not limited to, Antibody A-Antibody I can be made and purified essentially as follows. An appropriate host cell, such as HEK 293 or CHO, can be either transiently or stably transfected with an expression system for secreting antibodies using an optimal predetermined HC:LC vector ratio or a single vector system encoding both HC and LC. Clarified media, into which the antibody has been secreted, may be purified using any of many commonly-used techniques. For example, the medium may be conveniently applied to a MabSelect column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Antibody fractions may be detected, such as by SDS-PAGE, and then may be pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, multimodal, or hydroxyapatite chromatography. The purity of the antibody after these chromatography steps is greater than 95%. The product may be immediately frozen at −70° C. or may be lyophilized.

Table 1: SEQ ID NOs

TABLE 1

| SEQ ID NOs | | | |
|---|---|---|---|
| | Antibody A S228P IgG4 | Antibody B PAA IgG4 des-Lys | Antibody C VK1-12 IgG4 |
| HCVR | 12 | 12 | 12 |
| LCVR | 15 | 15 | 15 |
| Heavy chain | 16 | 19 | 23 |
| Light chain | 22 | 22 | 22 |
| | Antibody D S228P IgG4 | Antibody E PAA IgG4 des-Lys | Antibody F VK1-12 IgG4 |
| HCVR | 13 | 13 | 13 |
| LCVR | 15 | 15 | 15 |
| Heavy chain | 17 | 20 | 24 |
| Light chain | 22 | 22 | 22 |
| | Antibody G S228P IgG4 | Antibody H PAA IgG4 des-Lys | Antibody I VK1-12 IgG4 |
| HCVR | 14 | 14 | 14 |
| LCVR | 15 | 15 | 15 |
| Heavy chain | 18 | 21 | 25 |
| Light chain | 22 | 22 | 22 |

Assays

In Vivo Activity—WINN Assay

The antibodies of the present invention can be measured for in vivo immunomodulatory activity with the Winn assay. In the Winn assay, human tumor cells and human immune cells (allogenic) are injected together into an immunodeficient mouse, and then followed by dosing with an immunomodulatory agent. Tumor volume is measured to determine the effect of the agent in the assay.

Enhancement of the immune response to allo-antigens by antibodies of the present invention may be tested in the NCI-H292 human NSCLC xenograft model. On day 0, NSG mice from Jackson Laboratories (7 weeks of age, female, in groups of 8-10 mice) are implanted into the flank subcutaneously with either $2 \times 10^6$ H292 cells, or a mixture of $2 \times 10^6$ H292 cells and $1 \times 10^6$ human PBMCs in HBSS (0.2 ml total volume). Starting on Day 1, mice are treated with an i.p. injection of human IgG at 10 mg/kg, one time per week. Animal well-being and behavior, including grooming and ambulation are monitored at least twice per week. Body weight and tumor volume are measured twice a week.

In experiments performed essentially as described in this assay, Antibody A or Antibody D dosed at 10 mg/kg, qw, ip are well tolerated and safe as monitored by body weight and clinical observations. Tumor growth and T/C % results are shown in Table 2. Tumors in mice co-implanted with NCI-H292 and PBMCs and dosed with Antibody A or Antibody D at 10 mg/kg qw grew significantly slower and regressed over time. Under these conditions, Antibody A and Antibody D both mediate preferential enhanced alloreactivity compared to nivolumab and pembrolizumab.

TABLE 2

| WINN assay | | | | | | |
|---|---|---|---|---|---|---|
| | | Days Post Tumor Inoculation | | | | |
| | | 4 days | 7 days | 11 days | 14 days | 18 days |
| hIgG | Mean ± SEM | 22.5 ± 7.3 | 106.1 ± 14.5 | 322.2 ± 27.3 | 365.5 ± 36.7 | 838.8 ± 134.7 |
| hIgG + hPBMC | Mean ± SEM | 56.7 ± 11.5 | 170.7 ± 20.2 | 178.5 ± 15.7 | 157.9 ± 17.1 | 86.7 ± 16.2 |
| Nivolumab + hPBMC | Mean ± SEM | 61.0 ± 7.5 | 135.5 ± 11.2 | 215.8 ± 18.7 | 180.0 ± 31.8 | 93.5 ± 14.3 |
| | T/C % | 108% | 79% | 121% | 114% | 108% |
| Pembrolizumab + hPBMC | Mean ± SEM | 63.3 ± 5.4 | 145.0 ± 19.4 | 197.2 ± 22.1 | 144.9 ± 14.0 | 107.9 ± 15.9 |
| | T/C % | 112% | 85% | 110% | 92% | 125% |
| Antibody A + | Mean ± SEM | 29.7 ± 5.0 | 49.7 ± 5.9 | 89.1 ± 12.8 | 40.7 ± 9.8 | 31.1 ± 17.9 |

TABLE 2-continued

WINN assay

| | | Days Post Tumor Inoculation | | | | |
|---|---|---|---|---|---|---|
| | | 4 days | 7 days | 11 days | 14 days | 18 days |
| hPBMC | T/C % | 52% | 29% | 50% | 26% | 36% |
| Antibody D + hPBMC | Mean ± SEM | 31.9 ± 2.6 | 69.2 ± 6.6 | 99.8 ± 13.3 | 52.6 ± 12.3 | 21.9 ± 7.9 |
| | T/C % | 56% | 41% | 56% | 33% | 25% |

*T/C % is the ratio of tumor volume in control (hIgG + hPBMC) versus treated mice at a specified time.

Binding Kinetics and Affinity

The kinetics and equilibrium dissociation constant ($K_D$) for human PD-1 is determined for antibodies of the present invention using MSD, surface plasmon resonance (Biacore), and bio-layer interferometry (ForteBio) assay methods.

As used herein, nivolumab is a human IgG4 PD-1 antibody transiently expressed by applicants in 293 HEK cells that utilizes the heavy chain and light chain sequences from Proposed INN: List 107 (CAS #946414-94-4). As used herein, pembrolizumab is a human IgG4 PD-1 antibody transiently expressed by applicants in 293 HEK cells that utilizes the heavy chain and light chain sequences from Proposed INN: List 72.

MSD Assay

Equilibrium affinity measurements are performed as previously described (Estep, P., et al., MAbs, 2013. 5(2): p. 270-8). Solution equilibrium titrations (SET) are performed in PBS+0.1% IgG-Free BSA (PBSF) where antigen (b-PD-1 monomer) is held constant at 10-100 pM and is incubated with 3- to 5-fold serial dilutions of Fab or mAbs starting at 5-100 nM (experimental condition is sample dependent). Antibodies diluted at 20 nM in PBS are coated onto standard bind MSD-ECL plates overnight at 4° C. or at room temperature for 30 min. Plates are blocked with BSA for 30 min whilst shaking at 700 rpm. Plates are then washed 3× with wash buffer (PBSF+0.05% Tween 20). SET samples are applied and incubated on the plates for 150 s with shaking at 700 rpm followed by one wash. Antigen captured on a plate is detected with 250 ng/mL sulfotag-labeled streptavidin in PBSF by incubation on the plate for 3 min. The plates are washed three times with wash buffer and are then read on the MSD Sector Imager 2400 instrument using 1× Read Buffer T with surfactant. The percent free antigen is plotted as a function of titrated antibody in Prism and fit to a quadratic equation to extract the KD. To improve throughput, liquid handling robots are used throughout MSD-SET experiments, including for SET sample preparation.

In experiments performed essentially as described in this assay, Antibodies D and G in an IgG1 format and expressed in yeast, bind human PD-1 with a $K_D$ of 12 pM and 14 pM respectively. Pembrolizumab and nivolumab, both in an IgG1 format, bind PD-1 with a $K_D$ of 130 pM and 640 pM respectively. Avidity measurements for Antibodies D and G result in a $K_D$ of approximately 0.9 pM and 1 pM respectively. Pembrolizumab and nivolumab bind human PD-1 with a $K_D$ of approximately 3 pM and 5 pM respectively.

TABLE 3

Binding by MSD of antibodies of the invention in IgG1 format

| Name | Monovalent KD (pM) against human PD-1 | Avid KD (pM) against human PD-1 |
|---|---|---|
| Antibody D in IgG1 format | 12 | 0.9 |
| Antibody G in IgG1 format | 14 | 1 |
| Pembrolizumab (IgG1) | 130 | 3 |
| Nivolumab (IgG1) | 640 | 5 |

Bio-Layer Interferometry

ForteBio affinity measurements are performed generally as previously described (Estep, P., et al., *High throughput solution-based measurement of antibody-antigen affinity and epitope binning*. MAbs, 2013. 5(2): p. 270-8.). Briefly, ForteBio affinity measurements are performed by loading IgGs online onto AHQ sensors. Sensors are equilibrated off-line in assay buffer for 30 min and then monitored on-line for 60 seconds for baseline establishment. Sensors with loaded IgGs are exposed to 100 nM antigen for 5 min, afterwards they are transferred to assay buffer for 5 min for off-rate measurement. Kinetics are analyzed using the 1:1 binding model.

TABLE 4

Binding by Bio-layer interferometry of antibodies of the invention

| | Monovalent $K_D$ (pM) Fab in solution, hPD-1_Fc on sensor tip | Monovalent $K_D$ (pM) hPD-1_HIS in solution, IgG on sensor tip | Monovalent $K_D$ (pM) Fab in solution, cynoPD-1_Fc on sensor tip |
|---|---|---|---|
| Antibody D in IgG1 format | 560 | 310 | 670 |
| Antibody G in IgG1 format | 490 | 440 | 590 |
| Pembrolizumab in IgG1 format | 2000 | 2000 | 470 |
| Nivolumab in IgG1 format | 1700 | 4100 | 1200 |

In experiments performed essentially as described in this assay, Antibodies D and G bind human PD-1_Fc with a $K_D$ approximately threefold to fourfold lower than nivolumab and pembrolizumab when PD-1_Fc was on the sensor tip. When the antibody was on the sensor tip, Antibodies D and G bind human PD-1_Fc with a $K_D$ approximately fourfold to sixfold lower than nivolumab and pembrolizumab. Antibodies D and G bind cynoPD-1_Fc with a similar $K_D$ to nivolumab and pembrolizumab.

Surface Plasmon Resonance (SPR)

Immobilization of human PD-1-Fc (R&D Systems) as ligand on to sensor chip surface is performed at 25° C. Antibodies of the present invention are used as analyte, and injected over the human PD-1-Fc immobilized sensor chip surface. All sample analytes are run in 3-fold series dilutions from their starting concentration (90 nM), 8 total dilutions with one duplicate at a middle concentration and a zero. The analysis is performed at 37° C. The contact time for each sample is 180 sec at 30 µl/min. The dissociation time: 300 seconds for 5 lower concentrations and 1200 (Fab), or 2400 (T=0) or 3000 (4 weeks 4° C., 25° C., 40° C.) seconds for 3 higher concentrations. The immobilized surface is regenerated for 6-8 seconds with 0.4% SDS at 30 µl/min, and then stabilized for 5 seconds. Binding kinetics are analyzed using the Biacore T200 Evaluation software (Version 3.0). Data are referenced to a blank flow cell, and the data are fit to a 1:1 binding model.

In experiments performed essentially as described in this assay, Antibody D binds with a $K_D$ to human PD-1 of 102 pM, nivolumab with a $K_D$ of 246 pM, and pembrolizumab with a $K_D$ of 181 pM. As shown in Table 6, Antibody D maintained binding activity at 4 weeks under elevated temperature conditions.

TABLE 5

Binding by SPR of Antibody D at extended times and temperatures

| Binding to human PD-1-Fc | Kon (1/Ms) | Koff (1/s) | $K_D$ (pM) |
| --- | --- | --- | --- |
| Antibody D | 2.86E+05 | 2.98E−05 | 104 |
| Antibody D, 4 weeks 4° C. | 3.77E+05 | 3.86E−05 | 103 |
| Antibody D, 4 weeks 25° C. | 3.54E+05 | 3.60E−05 | 102 |
| Antibody D, 4 weeks 40° C. | 3.58E+05 | 4.22E−05 | 118 |

ELISA Blocking of Human PD-1 to PD-L1 and PD-L2.

For the receptor-ligand blocking assay, varying amounts (of anti-PD-1 antibody or control IgG are mixed with a fixed amount of biotinylated PD-1-Fc fusion protein (100 ng/mL) and incubated at room temperature for 1 hour. The mixture is transferred to 96-well plates pre-coated with PD-L1-Fc (100 ng/well) or PD-L2-Fc (100 ng/well) and then incubated at room temperature for an additional 1 hour. Plates are washed and streptavidin HRP conjugate is added. Plates are read at an absorbance at 450 nm. IC50 represents the antibody concentration required for 50% inhibition of PD-1 binding to PD-L1 or binding to PD-L2.

In experiments performed essentially as described, Antibody D blocks the interaction of PD-1 with PD-L1 with an IC50 of 0.30 nM, and the interaction of PD-1 with PD-L2 with an IC50 of 0.34 nM.

TABLE 6

Elisa Blocking Assay of human PD-1

| | Antibody D | Nivolumab | Pembrolizumab |
| --- | --- | --- | --- |
| Blocking PD-1/PD-L1 (IC50 nM) | 0.30 | 0.25 | 0.24 |
| Blocking PD-1/PD-L2 (IC50 nM) | 0.34 | 0.26 | 0.27 |

Binding to Human PD-1 on CHO Cells

The binding of an antibody of the present invention to human PD-1 may be measured in a flow cytometry assay.

CHO cells ($0.2 \times 10^6$) are incubated with antibody from 200 nM titrated 19× by a factor of 2 to the lowest concentration of 3.185 pM for 30 min in PBS 1% BSA on ice. Cells are then washed 3×, and are incubated with a secondary antibody (PE-labelled, at final concentration of 5 µg/ml) in PBS 1% BSA for 30 min on ice (protected from light). Cells are washed 3× and analyzed via flow cytometry. Flow cytometry is performed on an Accuri C6 system (BD Biosciences) and MFIs are calculated on the C6 software. EC50s are calculated on Graphpad software.

In experiments performed essentially as described in this assay, Antibody G binds PD-1 in a dose-dependent manner, with an EC50 value (n=1) of 1.756 nM and pembrolizumab binds PD-1 with an EC50 value (n=1) of 1.429 nM. Antibody D binds PD-1 in a dose-dependent manner, with an EC50 value (n=1) of 0.9784 nM, pembrolizumab with an EC50 value (n=1) of 0.9510 nM, and nivolumab with an EC50 value (n=1) of 0.9675 nM. Antibody D and Antibody G bind with a similar EC50 to human PD-1 as nivolumab and pembrolizumab under these conditions.

Blocking of Human PD-1 to PD-L2 in CHO Cells.

The ability of an antibody of the present invention to block binding of human PD-1 to PD-L1 and PD-L2 may be measured by flow cytometry.

CHO cells ($0.2 \times 10^6$) are incubated with the experimental antibody 100 nM for 30 mm in PBS 1% BSA on ice. Cells are then washed 3×, and are incubated with PD-L2 linked with NHS-Fluorescein (Promega) in PBS 1% BSA for 30 min on ice (protected from light). Cells are washed 3× and analyzed via flow cytometry. Flow cytometry is performed on an Accuri C6 system (BD Biosciences) and mean fluorescence intensity (MFI) is calculated on the C6 software.

In experiments performed essentially as described in this assay, Antibody D and G in IgG1 format, expressed in yeast, blocked human PD-L2-FITC binding, resulting in an MFI of 24,697.7 and 31,390.5 respectively as compared to control IgG which resulted in an MFI of 182,959.1. Pembrolizumab and nivolumab resulted in less blocking of PD-L2 binding to PD-1 than Antibody D and G with MFI's of 46,245.9 and 54,509.8, respectively.

TABLE 7

Blocking of human PD-1 on CHO cells

| Test Sample | MFI (PD-L2-FITC) |
| --- | --- |
| Cells only | 33,449.7 |
| No IgG | 199,716.0 |
| IgG Control | 182,959.1 |
| Nivolumab | 54,509.8 |
| Pembrolizumab | 46,245.9 |
| Antibody D in IgG1 format | 24,697.7 |
| Antibody G in IgG1 format | 31,390.5 |

Mixed Lymphocyte Reaction

The blocking of PD-1 signals by antibodies of the present invention may be evaluated by measuring the release of inhibitory signals during T cell activation. The levels of certain cytokines, such as IL-2, are expected to increase if T cell proliferation is promoted by treatment with antibodies of the present invention.

$2 \times 10^6$ PBMC are plated per well in a 6 well tissue culture plate or T25 tissue culture flask in complete T cell media. Cells are incubated for 2-3 hours, to allow for adherence of monocytes. If adherence is insufficient, serum free media is used. Unattached cells are removed by gently swirling the flask with fresh media 3×.

Immature myeloid DCs are generated by culturing monocytes ($1 \times 10^6$ cells/ml) from PBMC in X-VIVO 15 media containing 1% AB serum, 10 mM HEPES, 50 µM β-Me, IL-4 (1000 U/ml) and GM-CSF (1000 U/ml), or 25-50 ng/ml of each. After 2 days fresh medium supplemented with IL-4 and GM-CSF is added. On Day 5, cells are either frozen or maturation is induced by adding a stimulation cocktail containing rTNFa (1000 U/ml), IL-1b (5 ng/ml), IL-6 (10 ng/ml) and 1 μM $PGE_2$ for 2 days at a cell density of $3\times10^5$ cells/ml.

T cell Isolation is performed as per manufacturer's instructions in the Untouched CD4+ T cell isolation kit (Invitrogen). A magnet fitted with a 1.5 ml tube rack is used to remove unwanted magnetic beads (QIAGEN).

100,000-200,000 isolated T cells are mixed with 10,000-20,000 allogeneic moDCs in a total volume of 200 μl in 96-round bottom tissue culture plates for 4-5 days at 37° C. T cells are stimulated using anti-CD3/CD28 DynaBeads at a ratio of 3:1 (cells:beads) as a positive control; beads are prepared as per the manufacturer's instructions. Test antibodies are added at the beginning of the MLR and incubated throughout the culture period.

Detection of IL-2 and IFN-γ is carried out as per manufacturer's instructions (eBioscience). OD measurements are determined on a Multiskan FC system (Thermo).

In experiments performed essentially as described in this assay, Antibody D at each concentration increased IL-2 more than nivolumab and pembrolizumab. Antibody D and G resulted in a comparable increase of IFN-γ as nivolumab and pembrolizumab.

TABLE 8

IL-2 secretion fold change vs. IgG control

| | Concentrations of IgG | | | | |
|---|---|---|---|---|---|
| | 100 nM | 10 nM | 1 nM | 0.1 nM | 0.01 nM |
| Pembrolizumab | 2.03 | 2.49 | 2.04 | 1.47 | 1.06 |
| Nivolumab | 2.37 | 2.44 | 1.72 | 1.26 | 1.09 |
| Antibody D | 3.08 | 2.63 | 2.45 | 1.64 | 1.25 |
| Antibody G | 2.45 | 2.62 | 3.12 | 1.91 | 1.36 |

TABLE 9

IFN-γ secretion fold change vs. IgG control

| | Concentrations of IgG | | | | |
|---|---|---|---|---|---|
| | 100 nM | 10 nM | 1 nM | 0.1 nM | 0.01 nM |
| Pembrolizumab | 1.78 | 1.77 | 1.76 | 1.99 | 1.03 |
| Nivolumab | 1.97 | 1.88 | 1.58 | 1.53 | 0.84 |
| Antibody D | 1.72 | 1.99 | 2.26 | 1.94 | 1.32 |
| Antibody G | 2.07 | 2.04 | 2.48 | 1.91 | 1.17 |

Amino Acid and Nucleotide Sequences

SEQ ID NO: 1 (human PD-1)
MQIPQAPWPVVWAVLQLGWRPGWFLDSPDRPWNPPTFSPALLVVTEGDNATFT
CSFSNTSESFVLNWYRMSPSNQTDKLAAFPEDRSQPGQDCRFRVTQLPNGRDFH
MSVVRARRNDSGTYLCGAISLAPKAQIKESLRAELRVTERRAEVPTAHPSPSPRPA
GQFQTLVVGVVGGLLGSLVLLVWVLAVICSRAARGTIGARRTGQPLKEDPSAVP
VFSVDYGELDFQWREKTPEPPVPCVPEQTEYATIVFPSGMGTSSPARRGSADGPR
SAQPLRPEDGHCSWPL SEQ ID NO: 2 (HCDR1 of Antibody A, B, C, D, E, and F)
KASGGTFSSYAIS SEQ ID NO: 3 (HCDR1 of Antibody G, H, and I)
KASGGTLSSYAIS SEQ ID NO: 4 (HCDR2 of Antibody A, B, and C)
LIIPMFGTAGYAQKFQG SEQ ID NO: 5 (HCDR2 of Antibody D, E, and F)
LIIPMFDTAGYAQKFQG SEQ ID NO: 6 (HCDR2 of Antibody G, H, and I)
LIIPMFGAAGYAQRFQG SEQ ID NO: 7 (HCDR3 of Antibody A, B, and C)
ARAEYSSTGTFDY SEQ ID NO: 8 (HCDR3 of Antibody D, E, F, G, H, and I)
ARAEHSSTGTFDY SEQ ID NO: 9 (LCDR1 of Antibody A-Antibody I)
RASQGISSWLA SEQ ID NO: 10 (LCDR2 of Antibody A-Antibody I)
SAASSLQS SEQ ID NO: 11 (LCDR3 of Antibody A-Antibody I)
QQANHLPFT SEQ ID NO: 12 (HCVR of Antibody A, B, and C)
QVQLVQSGAEVKKPGSSVKVSCKASGGTFSSYAISWVRQAPGQGLEWMGLIIPM
FGTAGYAQKFQGRVTITADESTSTAYMELSSLRSEDTAVYYCARAEYSSTGTFDY
WGQGTLVTVSS SEQ ID NO: 13 (HCVR of Antibody D, E, and F)
QVQLVQSGAEVKKPGSSVKVSCKASGGTFSSYAISWVRQAPGQGLEWMGLIIPM
FDTAGYAQKFQGRVAITVDESTSTAYMELSSLRSEDTAVYYCARAEHSSTGTFD
YWGQGTLVTVSS

Amino Acid and Nucleotide Sequences

SEQ ID NO: 14 (HCVR of Antibody G, H, and I)
QVQLVQSGAEVKKPGSSVRVSCKASGGTLSSYAISWVRQAPGQGLEWMGLIIPM
FGAAGYAQRFQGRVTITADESASTAYMELSSLRSEDTAVYYCARAEHSSTGTFD
YWGQGTLVTVSS SEQ ID NO: 15 (LCVR of Antibody A-Antibody I)
DIQMTQSPSSVSASVGDRVTITCRASQGISSWLAWYQQKPGKAPKLLISAASSLQS
GVPSRFSGSGSGTDFTLTISSLQPEDFATYYCQQANHLPFTFGGGTKVEIK SEQ ID NO: 16 (HC of Antibody A-S228P IgG4)
QVQLVQSGAEVKKPGSSVKVSCKASGGTFSSYAISWVRQAPGQGLEWMGLIIPM
FGTAGYAQKFQGRVTITADESTSTAYMELSSLRSEDTAVYYCARAEYSSTGTFDY
WGQGTLVTVSSASTKGPSVFPLAPCSRSTSESTAALGCLVKDYFPEPVTVSWNSG
ALTSGVHTFPAVLQSSGLYSLSSVVTVPSSSLGTKTYTCNVDHKPSNTKVDKRVE
SKYGPPCPPCPAPEFLGGPSVFLFPPKPKDTLMISRTPEVTCVVVDVSQEDPEVQF
NWYVDGVEVHNAKTKPREEQFNSTYRVVSVLTVLHQDWLNGKEYKCKVSNKG
LPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYT
QKSLSLSLGK SEQ ID NO: 17 (HC of Antibody D-S228P IgG4)
QVQLVQSGAEVKKPGSSVKVSCKASGGTFSSYAISWVRQAPGQGLEWMGLIIPM
FDTAGYAQKFQGRVAITVDESTSTAYMELSSLRSEDTAVYYCARAEHSSTGTFD
YWGQGTLVTVSSASTKGPSVFPLAPCSRSTSESTAALGCLVKDYFPEPVTVSWNS
GALTSGVHTFPAVLQSSGLYSLSSVVTVPSSSLGTKTYTCNVDHKPSNTKVDKRV
ESKYGPPCPPCPAPEFLGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNK
GLPSSIEKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEALHNHY
TQKSLSLSLGK SEQ ID NO: 18 (HC of Antibody G-S228P IgG4)
QVQLVQSGAEVKKPGSSVRVSCKASGGTLSSYAISWVRQAPGQGLEWMGLIIPM
FGAAGYAQRFQGRVTITADESASTAYMELSSLRSEDTAVYYCARAEHSSTGTFD
YWGQGTLVTVSSASTKGPSVFPLAPCSRSTSESTAALGCLVKDYFPEPVTVSWNS
GALTSGVHTFPAVLQSSGLYSLSSVVTVPSSSLGTKTYTCNVDHKPSNTKVDKRV
ESKYGPPCPPCPAPEFLGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNK
GLPSSIEKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEALHNHY
TQKSLSLSLGK SEQ ID NO: 19 (HC of Antibody B-PAA IgG4 des-Lys)
QVQLVQSGAEVKKPGSSVKVSCKASGGTFSSYAISWVRQAPGQGLEWMGLIIPM
FGTAGYAQKFQGRVTITADESTSTAYMELSSLRSEDTAVYYCARAEYSSTGTFDY
WGQGTLVTVSSASTKGPSVFPLAPCSRSTSESTAALGCLVKDYFPEPVTVSWNSG
ALTSGVHTFPAVLQSSGLYSLSSVVTVPSSSLGTKTYTCNVDHKPSNTKVDKRVE
SKYGPPCPPCPAPEAAGGPSVFLFPPKPKDTLMISRTPEVTCVVVDVSQEDPEVQF
NWYVDGVEVHNAKTKPREEQFNSTYRVVSVLTVLHQDWLNGKEYKCKVSNKG
LPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYT
QKSLSLSLG SEQ ID NO: 20 (HC of Antibody E-PAA IgG4 des-Lys)
QVQLVQSGAEVKKPGSSVKVSCKASGGTFSSYAISWVRQAPGQGLEWMGLIIPM
FDTAGYAQKFQGRVAITVDESTSTAYMELSSLRSEDTAVYYCARAEHSSTGTFD
YWGQGTLVTVSSASTKGPSVFPLAPCSRSTSESTAALGCLVKDYFPEPVTVSWNS
GALTSGVHTFPAVLQSSGLYSLSSVVTVPSSSLGTKTYTCNVDHKPSNTKVDKRV
ESKYGPPCPPCPAPEAAGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNK
GLPSSIEKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEALHNHY
TQKSLSLSLG SEQ ID NO: 21 (HC of Antibody H-PAA IgG4 des-Lys)
QVQLVQSGAEVKKPGSSVRVSCKASGGTLSSYAISWVRQAPGQGLEWMGLIIPM
FGAAGYAQRFQGRVTITADESASTAYMELSSLRSEDTAVYYCARAEHSSTGTFD
YWGQGTLVTVSSASTKGPSVFPLAPCSRSTSESTAALGCLVKDYFPEPVTVSWNS
GALTSGVHTFPAVLQSSGLYSLSSVVTVPSSSLGTKTYTCNVDHKPSNTKVDKRV
ESKYGPPCPPCPAPEAAGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNK
GLPSSIEKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEALHNHY
TQKSLSLSLG

Amino Acid and Nucleotide Sequences

SEQ ID NO: 22 (LC of Antibody A-Antibody I)
DIQMTQSPSSVSASVGDRVTITCRASQGISSWLAWYQQKPGKAPKLLISAASSLQS
GVPSRFSGSGSGTDFTLTISSLQPEDFATYYCQQANHLPFTFGGGTKVEIKRTVAA
PSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC SEQ ID NO: 23 (HC of Antibody C-VK1-12 IgG4)
QVQLVQSGAEVKKPGSSVKVSCKASGGTFSSYAISWVRQAPGQGLEWMGLIIPM
FGTAGYAQKFQGRVTITADESTSTAYMELSSLRSEDTAVYYCARAEYSSTGTFDY
WGQGTLVTVSSASTKGPSVFPLAPCSRSTSESTAALGCLVKDYFPEPVTVSWNSG
ALTSGVHTFPAVLQSSGLYSLSSVVTVPSSSLGTKTYTCNVDHKPSNTKVDKRVE
SKYGPPCPSCPAPEFLGGPSVFLFPPKPKDTLMISRTPEVTCVVVDVSQEDPEVQF
NWYVDGVEVHNAKTKPREEQFNSTYRVVSVLTVLHQDWLNGKEYKCKVSNKG
LPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYT
QKSLSLSLGK SEQ ID NO: 24 (HC of Antibody F-VK1-12 IgG4)
QVQLVQSGAEVKKPGSSVKVSCKASGGTFSSYAISWVRQAPGQGLEWMGLIIPM
FDTAGYAQKFQGRVAITVDESTSTAYMELSSLRSEDTAVYYCARAEHSSTGTFD
YWGQGTLVTVSSASTKGPSVFPLAPCSRSTSESTAALGCLVKDYFPEPVTVSWNS
GALTSGVHTFPAVLQSSGLYSLSSVVTVPSSSLGTKTYTCNVDHKPSNTKVDKRV
ESKYGPPCPSCPAPEFLGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNK
GLPSSIEKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEALHNHY
TQKSLSLSLGK SEQ ID NO: 25 (HC of Antibody I-VK1-12 IgG4)
QVQLVQSGAEVKKPGSSVRVSCKASGGTLSSYAISWVRQAPGQGLEWMGLIIPM
FGAAGYAQRFQGRVTITADESASTAYMELSSLRSEDTAVYYCARAEHSSTGTFD
YWGQGTLVTVSSASTKGPSVFPLAPCSRSTSESTAALGCLVKDYFPEPVTVSWNS
GALTSGVHTFPAVLQSSGLYSLSSVVTVPSSSLGTKTYTCNVDHKPSNTKVDKRV
ESKYGPPCPSCPAPEFLGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNK
GLPSSIEKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEALHNHY
TQKSLSLSLGK SEQ ID NO: 26 (DNA of HC of Antibody A-S228P IgG4)
CAGGTGCAGCTGGTGCAGAGCGGCGCTGAGGTGAAGAAGCCTGGCTCCAGCG
TGAAGGTGTCCTGCAAAGCCTCCGGCGGCACCTTCAGCTCCTACGCTATCAGC
TGGGTGAGGCAGGCTCCTGGCCAGGGACTGGAGTGGATGGGCCTGATCATCC
CCATGTTCGGCACCGCTGGCTACGCCCAGAAGTTCCAGGGCAGGGTGACCAT
CACCGCCGACGAGTCCACCTCACCGCCTACATGGAGCTGTCCTCCCTGAGGT
CCGAGGACACCGCCGTGTACTACTGTGCCAGGGCCGAGTACTCCTCCACCGG
CACCTTCGACTACTGGGGCCAGGGCACACTCGTGACCGTCAGCTCCGCCAGC
ACAAAGGGCCCCAGCGTGTTTCCCCTGGCCCCTTGCAGCAGGAGCACATCCG
AGAGCACCGCTGCCCTGGGATGTCTGGTGAAGGACTATTTCCCCGAGCCCGT
GACAGTGAGCTGGAACAGCGGAGCCCTGACCTCCGGAGTGCACACCTTCCCT
GCCGTGCTGCAGAGCAGCGGACTGTACAGCCTGTCCAGCGTGGTGACAGTGC
CTTCCTCCAGCCTCGGCACAAAGACCTACACCTGCAACGTGGACCACAAGCC
CTCCAACACCAAAGTGGACAAGCGGGTGGAAAGCAAGTATGGACCCCCCTTGC
CCTCCTTGTCCCGCCCCTGAGTTCCTGGGAGGCCCTTCCGTCTTCCTGTTTCCC
CCCAAGCCCAAGGACACACTCATGATTTCCAGGACCCCCGAGGTGACCTGCG
TCGTGGTCGACGTGAGCCAGGAGGACCCCGAGGTGCAGTTTAACTGGTATGT
GGACGGCGTGGAGGTCCACAATGCCAAAACCAAGCCCAGGGAGGAACAGTT
CAACTCCACCTATAGGGTGGTCAGCGTGCTGACCGTCCTGCACCAGGACTGG
CTGAACGGAAAGGAGTATAAGTGCAAAGTCTCCAACAAGGGCCTGCCTAGCA
GCATCGAGAAGACCATCTCCAAAGCCAAGGGCCAGCCCAGGGAGCCCCAGGT
TTATACTCTGCCCCCTTCCCAGGAGGAGATGACCAAGAATCAGGTGTCCCTGA
CCTGCCTGGTGAAAGGCTTTTACCCCTCCGACATCGCTGTGGAGTGGGAGAGC
AATGGCCAGCCCGAGAACAACTACAAGACCACCCCCCCCGTGCTGGATAGCG
ATGGCAGCTTCTTCCTCTACAGCAGGCTGACCGTGGATAAGAGCAGGTGGCA
GGAGGGCAACGTGTTTTCCTGCTCCGTGATGCATGAGGCCCTCCACAACCATT
ACACACAGAAAAGCCTGAGCCTGAGCCTGGGCAAGTGATGA SEQ ID NO: 27 (DNA of HC of Antibody D-S228P IgG4)
CAAGTGCAGCTGGTGCAGTCCGGCGCTGAGGTGAAAAAACCCGGATCCTCCG
TCAAGGTGTCCTGTAAAGCCAGCGGCGGCACATTCAGCAGCTACGCCATCTC
CTGGGTGAGGCAAGCTCCTGGACAGGGCCTGGAATGGATGGGCCTGATCATC
CCCATGTTCGACACCGCCGGCTACGCTCAGAAATTCCAGGGCCGGGTCGCCA
TTACAGTGGATGAGAGCACCAGCACAGCCTACATGGAGCTCAGCTCCCTGAG
GAGCGAAGATACCGCCGTCTACTATTGTGCCCGGGCTGAGCATAGCAGCACC
GGCACCTTCGACTATTGGGGCCAGGGAACCCTGGTCACAGTGAGCTCCGCTTC
CACAAAAGGCCCCAGCGTGTTTCCCCTGGCCCCTTGTAGCAGGTCCACCTCCG

| Amino Acid and Nucleotide Sequences |
| --- |
| AAAGCACAGCCGCTCTGGGCTGCCTGGTCAAGGATTACTTCCCCGAGCCCGT
GACCGTGTCCTGGAATAGCGGCGCTCTCACATCCGGAGTGCATACCTTTCCTG
CCGTGCTCCAGTCCTCCGGCCTGTACTCCCTGAGCTCCGTGGTGACCGTCCCT
TCCAGCTCCCTGGGCACCAAGACCTATACCTGTAACGTGGACCACAAGCCCTC
CAATACCAAGGTGGATAAGCGGGTCGAGTCCAAGTACGGACCCCCTTGCCCT
CCTTGTCCTGCTCCTGAATTCCTCGGCGGACCTAGCGTCTTTCTCTTCCCCCCC
AAGCCCAAGGATACCCTGATGATCTCCAGGACCCCCGAGGTGACATGCGTCG
TGGTCGATGTGTCCCAGGAGGATCCTGAAGTGCAGTTCAACTGGTACGTGGA
CGGCGTCGAAGTGCATAACGCCAAGACCAAGCCCAGGGAGGAGCAGTTCAA
CTCCACCTATCGGGTGGTGAGCGTGCTGACCGTGCTGCATCAGGACTGGCTCA
ACGGCAAAGAGTACAAGTGCAAGGTCTCCAACAAGGGACTCCCCTCCAGCAT
CGAGAAGACCATTAGCAAGGCCAAAGGCCAACCCAGGGAGCCTCAGGTATAT
ACGCTGCCCCCCAGCCAGGAGGAGATGACCAAAAACCAGGTCAGCCTCACCT
GTCTGGTCAAGGGCTTCTACCCTAGCGACATTGCTGTCGAGTGGGAGAGCAA
CGGCCAGCCCGAGAACAACTATAAAACCACCCCCCCTGTCCTGGACTCCGAC
GGATCCTTCTTCCTGTACTCCAGGCTGACAGTCGACAAGTCCCGGTGGCAAGA
GGGAAACGTCTTCTCCTGCTCCGTGATGCACGAAGCTCTCCACAACCACTACA
CCCAGAAGAGCCTCAGCCTGTCCCTGGGCAAATGATGA SEQ ID NO: 28 (DNA of HC of Antibody G-S228P IgG4)
CAAGTCCAGCTCGTGCAAAGCGGAGCCGAGGTGAAGAAACCCGGCAGCTCCG
TGCGGGTGAGCTGTAAGGCCTCCGGAGGCACCCTGTCCAGCTATGCTATCAG
CTGGGTGAGGCAGGCCCCCGGACAGGGCCTGGAATGGATGGGACTGATCATC
CCTATGTTTGGAGCCGCCGGCTATGCTCAGAGGTTCCAGGGCCGGGTCACCAT
CACCGCTGACGAGAGCGCCAGCACCGCCTATATGGAGCTGTCCTCCCTGAGG
AGCGAGGATACCGCTGTCTACTACTGTGCCAGGGCCGAGCACTCCTCCACAG
GAACCTTCGACTACTGGGGCCAGGGCACCCTGGTGACAGTGTCCTCCGCCTCC
ACCAAGGGCCCCTTCCGTGTTTCCTCTGGCTCCTTGCTCCCGGTCCACCAGCGA
GTCCACAGCCGCTCTGGGCTGTCTGGTGAAGGACTATTTCCCCGAGCCTGTGA
CCGTCAGCTGGAATAGCGGCGCCCTGACCTCCGGAGTGCACACATTCCCCGC
CGTCCTGCAGAGCAGCGGACTCTACTCCCTGAGCTCCGTGGTGACCGTGCCTT
CCAGCAGCCTGGGAACCAAGACCTACACCTGCAATGTGGACCACAAACCCAG
CAACACCAAGGTGGATAAGCGGGTGGAATCCAAGTACGGCCCTCCCTGTCCC
CCTTGTCCCGCTCCCGAATTCCTGGGCGGACCTAGCGTGTTCCTGTTTCCCCCT
AAGCCCAAGGATACCCTGATGATCTCCAGGACCCCCGAAGTCACCTGCGTCG
TCGTGGACGTGTCCCAGGAGGACCCTGAAGTCCAGTTTAATTGGTACGTCGAC
GGCGTGGAGGTGCACAACGCCAAGACAAAGCCTCGGGAGGAGCAGTTCAAC
AGCACCTACAGGGTGGTGAGCGTGCTGACCGTGCTGCACCAGGACTGGCTGA
ACGGCAAAGAGTACAAGTGCAAGGTGAGCAACAAGGGCCTGCCCTCCTCCAT
CGAGAAGACCATCTCCAAGGCCAAAGGCCAGCCGAGGGAGCCCCAGGTGTA
CACCCTGCCCCCTAGCCAGGAGGAGATGACCAAGAACCAGGTCTCCCTGACC
TGCCTGGTGAAGGGATTCTATCCCAGCGACATTGCCGTGGAGTGGGAGTCCA
ACGGCCAGCCCGAGAATAACTACAAGACCACCCCCCCTGTGCTGGACAGCGA
CGGGAGCTTCTTCCTGTATTCCCGGCTGACCGTCGACAAGTCCCGGTGGCAGG
AGGGCAACGTGTTTAGCTGCAGCGTGATGCACGAAGCCCTCCACAACCACTA
TACCCAGAAGAGCCTGTCCCTGTCCCTGGGCAAGTGATGA SEQ ID NO: 29 (DNA of HC of Antibody E-PAA IgG4 des-Lys)
CAGGTGCAGCTGGTCCAGTCAGGGGCTGAAGTGAAGAAGCCCGGCAGCTCCG
TGAAGGTGTCTTGCAAGGCCAGCGGCGGAACATTCTCCAGTTACGCCATCTCT
TGGGTGCGGCAGGCTCCAGGCCAGGGCCTGGAGTGGATGGGCCTGATCATCC
CCATGTTCGACACCGCCGGGTATGCCCAGAAGTTTCAGGGCAGAGTGGCAAT
CACCAGTGGACGAGAGCACCTCCACAGCCTACATGGAGCTGTCTAGCCTGAGA
TCCGAGGATACCGCCGTGTATTATTGTGCCCGGGCCGAACACAGCTCTACAG
GGACTTTCGACTACTGGGGCCAGGGCACCCTGGTGACAGTGTCCTCTGCTAGC
ACCAAGGGCCCATCGGTCTTCCCGCTCGCGCCCTGCTCCAGGAGCACCTCCGA
GAGCACAGCCGCCCTGGGCTGCCTGGTCAAGGACTACTTCCCCGAACGGGTG
ACGGTGTCGTGGAACTCAGGCGCCCTGACCAGCGGCGTGCACACCTTCCCGG
CTGTCCTACAGTCCTCAGGACTCTACTCCCTCAGCAGCGTGGTGACCGTGCCC
TCCAGCAGCTTGGGCACGAAGACCTACACCTGCAACGTAGATCACAAGCCCA
GCAACACCAAGGTGGACAAGAGAGTTGAGTCCAAATATGGTCCCCCATGCCC
ACCCTGCCCAGCACCTGAGGCCGCCGGGGGACCATCAGTCTTCCTGTTCCCCC
CAAAACCCAAGGACACTCTCATGATCTCCCGGACCCCTGAGGTCACGTGCGT
GGTGGTGGACGTGAGCCAGGAAGACCCCGAGGTCCAGTTCAACTGGTATGTT
GATGGCGTGGAGGTGCATAATGCCAAGACAAAGCCGCGGGAGGAGCAGTTC
AACAGCACGTACCGTGTGGTCAGCGTCCTCACCGTCCTGCACCAGGACTGGCT
GAACGGCAAGGAGTACAAGTGCAAGGTCTCCAACAAAGGCCTCCCGTCCTCC
ATCGAGAAAACCATCTCCAAAGCCAAAGGGCAGCCCCGAGAGCCACAGGTGT
ACACCCTGCCCCCATCCCAAGAAGAAATGACCAAAAACCAAGTCAGCCTGAC
CTGCCTGGTCAAAGGCTTCTACCCCAGCGACATCGCCGTGGAGTGGGAAAGC
AATGGGCAGCCGGAGAACAACTACAAGACCACGCCTCCCGTGCTGGACTCCG
ACGGCTCCTTCTTCCTCTACTCCCGTCTAACCGTGGACAAGAGCAGGTGGCAG
GAGGGGAATGTCTTCTCATGCTCCGTGATGCATGAGGCTCTGCAACCACTA
CACACAGAAGAGCCTCTCCCTGTCTCTGGGT |

| Amino Acid and Nucleotide Sequences |
|---|
| SEQ ID NO: 30 (DNA of LC of Antibody A-Antibody I)<br>GACATCCAGATGACACAGTCCCCTAGCTCCGTGTCCGCTTCCGTGGGAGACA<br>GGGTGACAATCACATGCAGGGCTTCCCAGGGCATCAGCAGCTGGCTGGCTTG<br>GTATCAGCAGAAGCCCGGCAAGGCCCCCAAGCTGCTGATCAGCGCTGCTAGC<br>TCCCTGCAGTCCGGAGTGCCTTCCAGGTTCTCCGGCTCCGGAAGCGGCACCGA<br>CTTCACCCTGACCATCTCCAGCCTGCAGCCCGAGGACTTCGCCACCTACTACT<br>GCCAACAGGCCAACCACCTGCCCTTCACCTTCGGCGGCACCAAGGTGGA<br>GATCAAGAGGACCGTGGCCGCCCCCTCCGTGTTCATCTTTCCCCCAGCGACG<br>AGCAGCTGAAGAGCGGCACCGCCTCCGTGGTGTGCCTGCTGAACAACTTCTA<br>TCCCCGGGAGGCCAAGGTGCAGTGGAAGGTCGACAATGCCCTGCAGAGCGGC<br>AACTCCCAGGAGAGCGTGACCGAGCAGGACAGCAAGGACTCCACCTACTCCC<br>TGAGCTCCACCCTGACACTGTCCAAGGCCGACTACGAGAAGCACAAGGTGTA<br>CGCCTGCGAGGTGACACACCAGGGCCTGAGCTCCCCCGTGACCAAGTCCTTC<br>AACAGGGGCGAGTGCTGATGA |

We claim:

1. An antibody that binds human PD-1 (SEQ ID NO: 1), comprising a light chain (LC) and a heavy chain (HC), wherein the light chain comprises light chain complementarity determining regions LCDR1, LCDR2, and LCDR3 consisting of the amino acid sequences RASQGISSWLA (SEQ ID NO: 9), SAASSLQS (SEQ ID NO: 10), and QQANHLPFT (SEQ ID NO: 11), respectively, and wherein the heavy chain comprises heavy chain complementarity determining regions HCDR1, HCDR2, and HCDR3, wherein HCDR1 consists of the amino acid sequences KASGGTFSSYAIS (SEQ ID NO: 2) or KASGGTLSSYAIS (SEQ ID NO: 3), wherein HCDR2 consists of the amino acid sequences LIIPMFGTAGYAQKFQG (SEQ ID NO: 4), LIIPMFDTAGYAQKFQG (SEQ ID NO: 5) or LIIPMFGAAGYAQRFQG (SEQ ID NO: 6), and wherein HCDR3 consists of the amino acid sequences ARAEYSSTGTFDY (SEQ ID NO: 7) or ARAEHSSTGTFDY (SEQ ID NO:8).

2. The antibody of claim 1, wherein LCDR1, LCDR2, and LCDR3 consist of the amino acid sequences RASQGISSWLA (SEQ ID NO: 9), SAASSLQS (SEQ ID NO: 10), and QQANHLPFT (SEQ ID NO: 11), respectively, and wherein HCDR1, HCDR2, and HCDR3 consist of the amino acid sequences KASGGTFSSYAIS (SEQ ID NO: 2), LIIPMFGTAGYAQKFQG (SEQ ID NO: 4), and ARAEYSSTGTFDY (SEQ ID NO: 7), respectively.

3. The antibody of claim 1, wherein LCDR1, LCDR2, and LCDR3 consist of the amino acid sequences RASQGISSWLA (SEQ ID NO: 9), SAASSLQS (SEQ ID NO:10), and QQANHLPFT (SEQ ID NO: 11), respectively, and wherein HCDR1, HCDR2, and HCDR3 consist of the amino acid sequences KASGGTFSSYAIS (SEQ ID NO: 2), LIIPMFDTAGYAQKFQG (SEQ ID NO: 5), and ARAEHSSTGTFDY (SEQ ID NO: 8), respectively.

4. The antibody of claim 1, wherein LCDR1, LCDR2, and LCDR3 consist of the amino acid sequences RASQGISSWLA (SEQ ID NO: 9), SAASSLQS (SEQ ID NO:10), and QQANHLPFT (SEQ ID NO: 11), respectively, and wherein HCDR1, HCDR2, and HCDR3 consist of the amino acid sequences KASGGTLSSYAIS (SEQ ID NO: 3), LIIPMFGAAGYAQRFQG (SEQ ID NO: 6), and ARAEHSSTGTFDY (SEQ ID NO: 8), respectively.

5. An antibody that binds human PD-1 (SEQ ID NO: 1), comprising a light chain (LC) and a heavy chain (HC), wherein the light chain comprises a light chain variable region (LCVR) and the heavy chain comprises a heavy chain variable region (HCVR), wherein the LCVR has the amino acid sequence given in SEQ ID NO: 15, and the HCVR has the amino acid sequence given in SEQ ID NO: 12, SEQ ID NO: 13, or SEQ ID NO: 14.

6. The antibody of claim 5, wherein the LCVR has the amino acid sequence given in SEQ ID NO: 15, and the HCVR has the amino acid sequence given in SEQ ID NO: 12.

7. The antibody of claim 5, wherein the LCVR has the amino acid sequence given in SEQ ID NO: 15, and the HCVR has the amino acid sequence given in SEQ ID NO: 13.

8. The antibody of claim 5, wherein the LCVR has the amino acid sequence given in SEQ ID NO: 15, and the HCVR has the amino acid sequence given in SEQ ID NO: 14.

9. The antibody of claim 5, wherein the LC has the amino acid sequence given in SEQ ID NO: 22, and the HC has the amino acid sequence given in SEQ ID NO: 16, SEQ 11 NO: 17, SEQ ID NO: 18, SEQ ID NO: 19, SEQ ID NO:20, or SEQ ID NO: 21.

10. The antibody of claim 9, wherein the LC has the amino acid sequence given in SEQ ID NO: 22, and the HC has the amino acid sequence given in SEQ ID NO: 16.

11. The antibody of claim 9, wherein the LC has the amino acid sequence given in SEQ ID NO: 22, and the HC has the amino acid sequence given in SEQ ID NO: 17.

12. The antibody of claim 9, wherein the LC has the amino acid sequence given in SEQ ID NO: 22, and the HC has the amino acid sequence given in SEQ ID NO: 18.

13. The antibody of claim 9, wherein the LC has the amino acid sequence given in SEQ ID NO: 22, and the HC has the amino acid sequence given in SEQ ID NO: 19.

14. The antibody of claim 9, wherein the LC has the amino acid sequence given in SEQ ID NO: 22, and the HC has the amino acid sequence given in SEQ ID NO: 20.

15. The antibody of claim 9, wherein the LC has the amino acid sequence given in SEQ ID NO: 22, and the HC has the amino acid sequence given in SEQ ID NO: 21.

16. The antibody of claim 9, comprising two light chains and two heavy chains, wherein each light chain has the amino acid sequence given in SEQ ID NO: 22, and each heavy chain has the amino acid sequence given in SEQ ID NO: 16, SEQ ID NO: 17, SEQ ID NO: 18, SEQ ID NO: 19, SEQ ID NO: 20, or SEQ ID NO: 21.

17. The antibody of claim 16, wherein each light chain has the amino acid sequence given in SEQ ID NO: 22, and each heavy chain has the amino acid sequence given in SEQ ID NO: 16.

18. The antibody of claim 16, wherein each light chain has the amino acid sequence given in SEQ ID NO: 22, and each heavy chain has the amino acid sequence given in SEQ ID NO: 17.

19. The antibody of claim 16, wherein each light chain has the amino acid sequence given in SEQ ID NO: 22, and each heavy chain has the amino acid sequence given in SEQ ID NO: 18.

20. The antibody of claim 16, wherein each light chain has the amino acid sequence given in SEQ ID NO: 22, and each heavy chain has the amino acid sequence given in SEQ ID NO: 19.

21. The antibody of claim 16, wherein each light chain has the amino acid sequence given in SEQ ID NO: 22, and each heavy chain has the amino acid sequence given in SEQ ID NO: 20.

22. The antibody of claim 16, wherein each light chain has the amino acid sequence given in SEQ ID NO: 22, and each heavy chain has the amino acid sequence given in SEQ ID NO: 21.

23. The antibody of claim 5, wherein one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain.

24. The antibody of claim 23, wherein the antibody is glycosylated.

25. A mammalian cell comprising a DNA molecule comprising a polynucleotide sequence encoding a polypeptide having an amino acid sequence of SEQ ID NO: 22 and a polynucleotide sequence encoding a polypeptide having an amino acid sequence of SEQ ID NO: 17 or SEQ ID NO:20, wherein the cell is capable of expressing an antibody comprising alight chain having an amino acid sequence of SEQ ID NO: 22 and a heavy chain having an amino acid sequence of SEQ ID NO: 17 or SEQ ID NO: 20 wherein the antibody binds human PD-1 (SEQ ID NO: 1).

26. A process for producing an antibody comprising a light chain having an amino acid sequence of SEQ ID NO: 22 and a heavy chain having an amino acid sequence of SEQ ID NO: 17 or SEQ ID NO: 20, comprising cultivating the mammalian cell of claim 25 under conditions such that the antibody is expressed, and recovering the expressed antibody wherein the antibody binds human PD-1 (SEQ ID NO:1).

27. An antibody produced by the process of claim 26.

28. A pharmaceutical composition, comprising the antibody of claim 1, and an acceptable carrier, diluent, or excipient.

29. A method of treating cancer, comprising administering to a patient in need thereof, an effective amount of the antibody of claim 1.

30. The method of claim 29, wherein the cancer is melanoma, lung cancer, head and neck cancer, colorectal cancer, pancreatic cancer, gastric cancer, kidney cancer, bladder cancer, prostate cancer, breast cancer, ovarian cancer, or hepatocellular carcinoma.

31. The method of claim 30, further comprising administering simultaneously, separately, or sequentially one or more anti-tumor agents.

* * * * *